(12) United States Patent
Sala et al.

(10) Patent No.: US 7,722,612 B2
(45) Date of Patent: May 25, 2010

(54) DEVICES, KIT AND METHOD FOR KYPHOPLASTY

(75) Inventors: Giuseppe Sala, Desio (IT); Paolo Guerra, Milan (IT); Domenico Prestamburgo, Vareis (IT); Michele Surace, Milan (IT)

(73) Assignee: Sintea Biotech S.p.A., Milan (IT)

( * ) Notice: Subject to any disclaimer, the term of this patent is extended or adjusted under 35 U.S.C. 154(b) by 1304 days.

(21) Appl. No.: 10/502,717

(22) PCT Filed: May 19, 2004

(86) PCT No.: PCT/IT2004/000289

§ 371 (c)(1),
(2), (4) Date: Jul. 29, 2004

(87) PCT Pub. No.: WO2005/110259

PCT Pub. Date: Nov. 24, 2005

(65) Prior Publication Data
US 2006/0235417 A1 Oct. 19, 2006

(51) Int. Cl.
A61B 17/00 (2006.01)
(52) U.S. Cl. ...................................................... 606/79
(58) Field of Classification Search ............... 606/79, 606/63, 313, 327, 81, 86 R, 170, 180, 182, 606/183, 232
See application file for complete search history.

(56) References Cited

U.S. PATENT DOCUMENTS

| 5,030,201 | A | * | 7/1991 | Palestrant | 604/22 |
| 5,059,193 | A | * | 10/1991 | Kuslich | 606/247 |
| 5,795,322 | A | * | 8/1998 | Boudewijn | 604/22 |
| 6,224,600 | B1 | * | 5/2001 | Protogirou | 606/63 |
| 6,436,140 | B1 | * | 8/2002 | Liu et al. | 623/17.11 |
| 6,740,090 | B1 | * | 5/2004 | Cragg et al. | 606/79 |
| 6,893,450 | B2 | * | 5/2005 | Foster | 606/200 |
| 7,172,609 | B2 | * | 2/2007 | Radisch, Jr. | 606/159 |
| 2002/0026197 | A1 | | 2/2002 | Foley et al. | |
| 2002/0165544 | A1 | * | 11/2002 | Perren et al. | 606/63 |
| 2004/0133204 | A1 | * | 7/2004 | Davies | 606/63 |

* cited by examiner

*Primary Examiner*—Thomas C Barrett
*Assistant Examiner*—Michael J Araj
(74) *Attorney, Agent, or Firm*—Hogan & Hartson LLP

(57) ABSTRACT

An intravertebral widening device (4) extends from a proximal end (8) to a distal end (10) along an extension axis (X), said distal end (10) having an elastically deformable element (56) suitable to pass from a relaxed configuration for placing the distal end (10) within a vertebral body (6) to a deformed configuration for forming a cavity within said vertebral body (6). The elastically deformable element (56) comprises at least one tab (60) having, along the longitudinal extension thereof, a varying thickness relative to a radial direction incident with said extension axis (X) and contained in a perpendicular plane to said extension axis (X), such as to vary the stiffness of at least one tab (60) along the extension thereof.

17 Claims, 20 Drawing Sheets

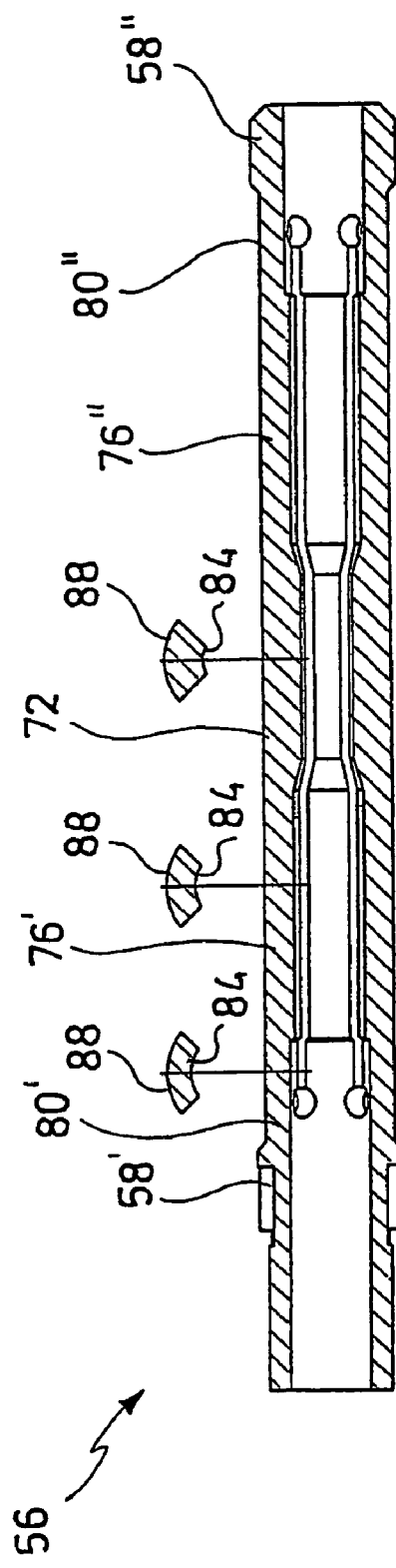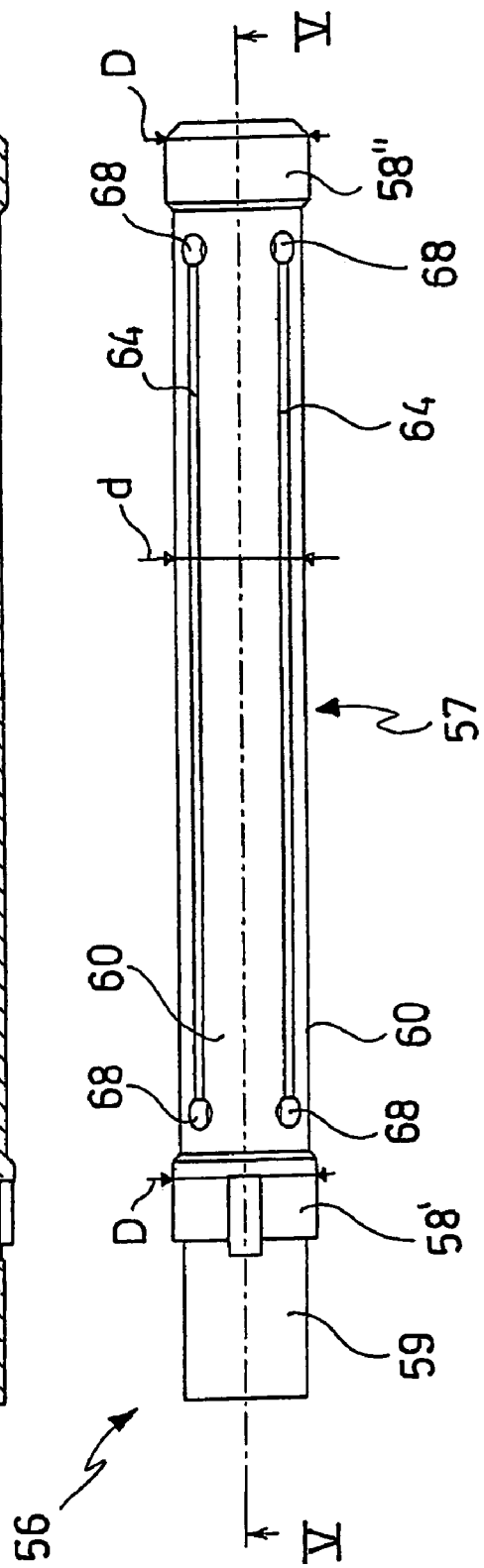

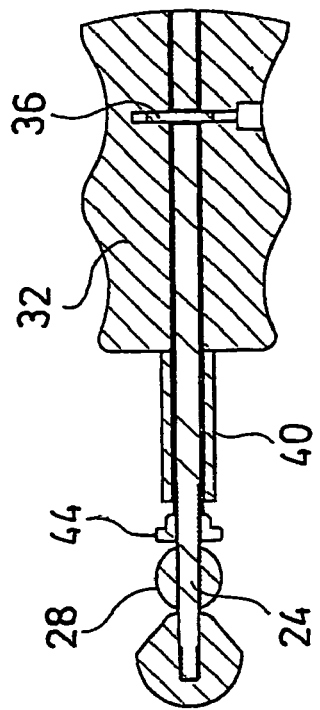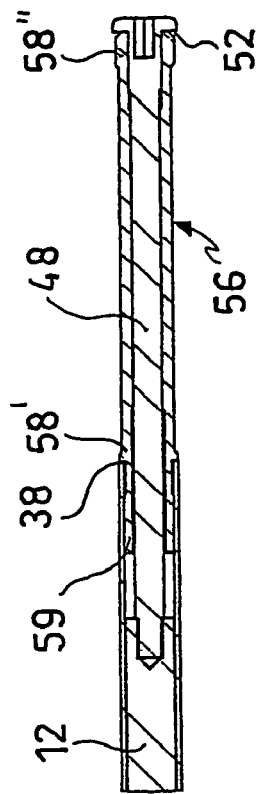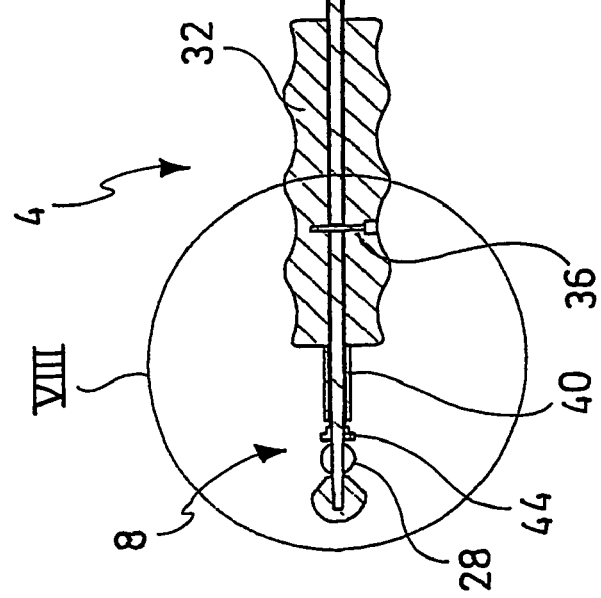

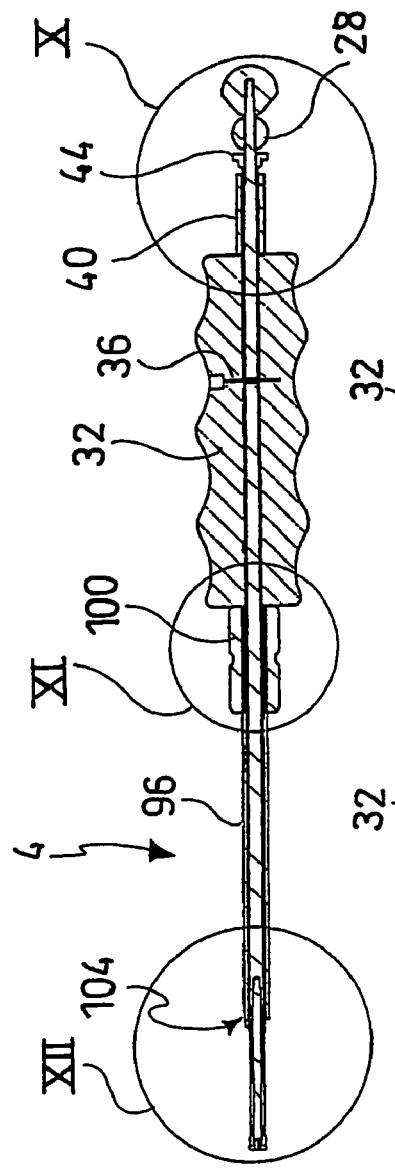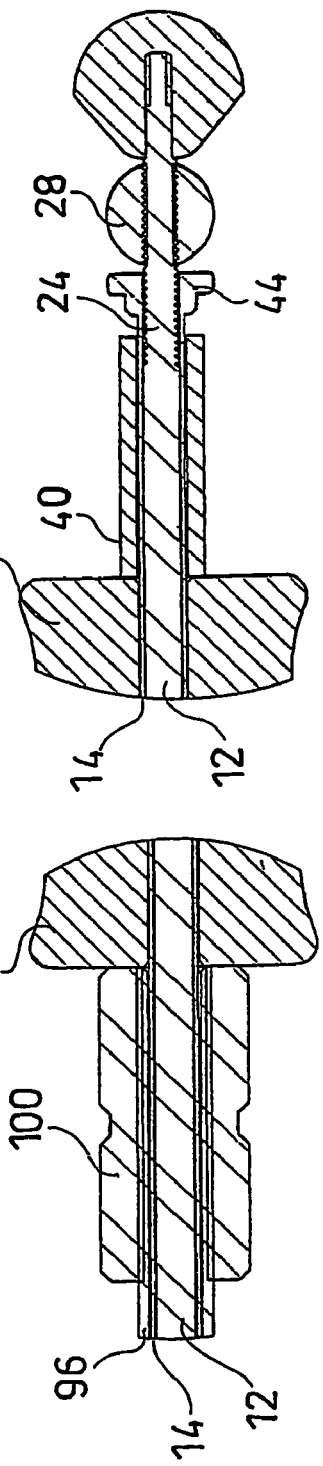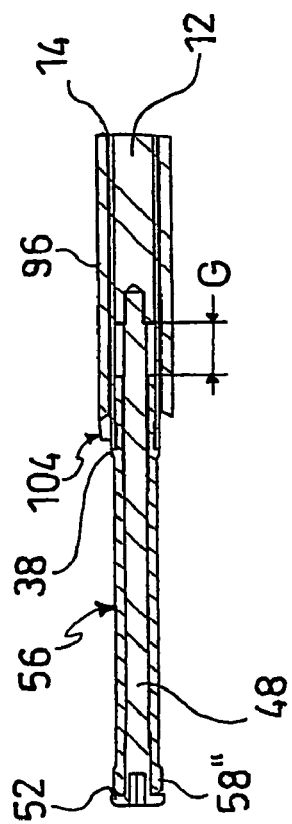
FIG.9
FIG.10
FIG.11
FIG.12

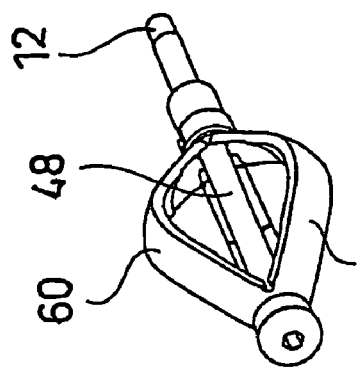
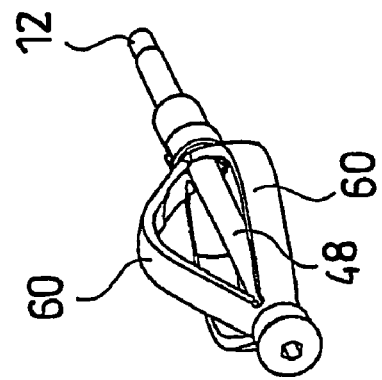
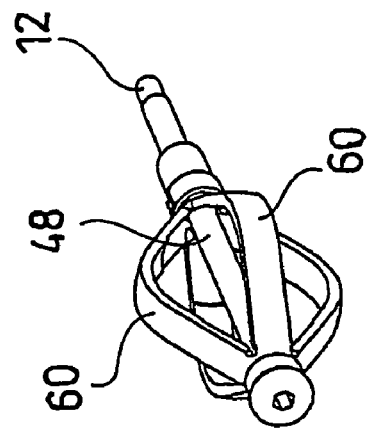
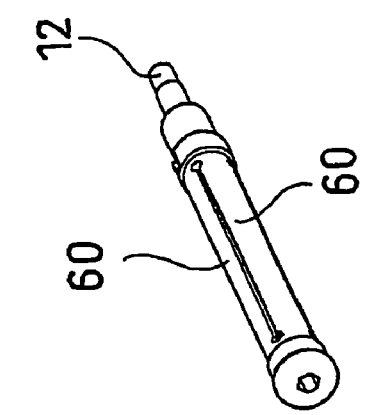
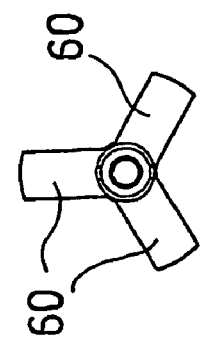
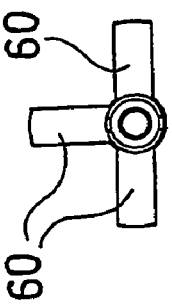
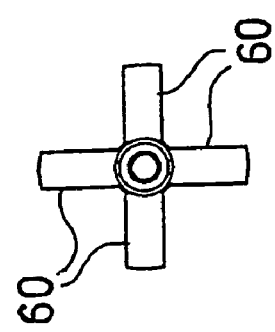

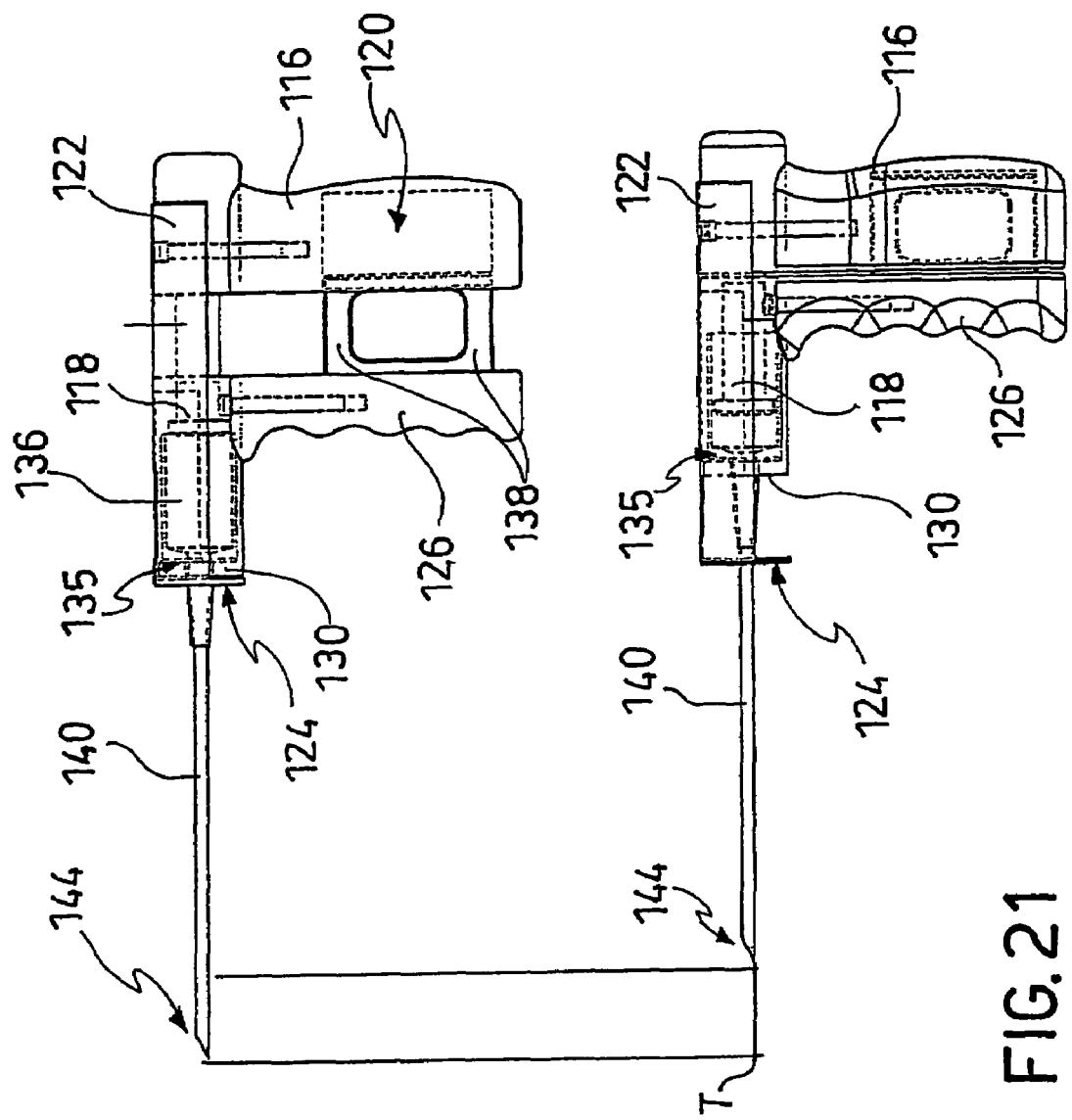

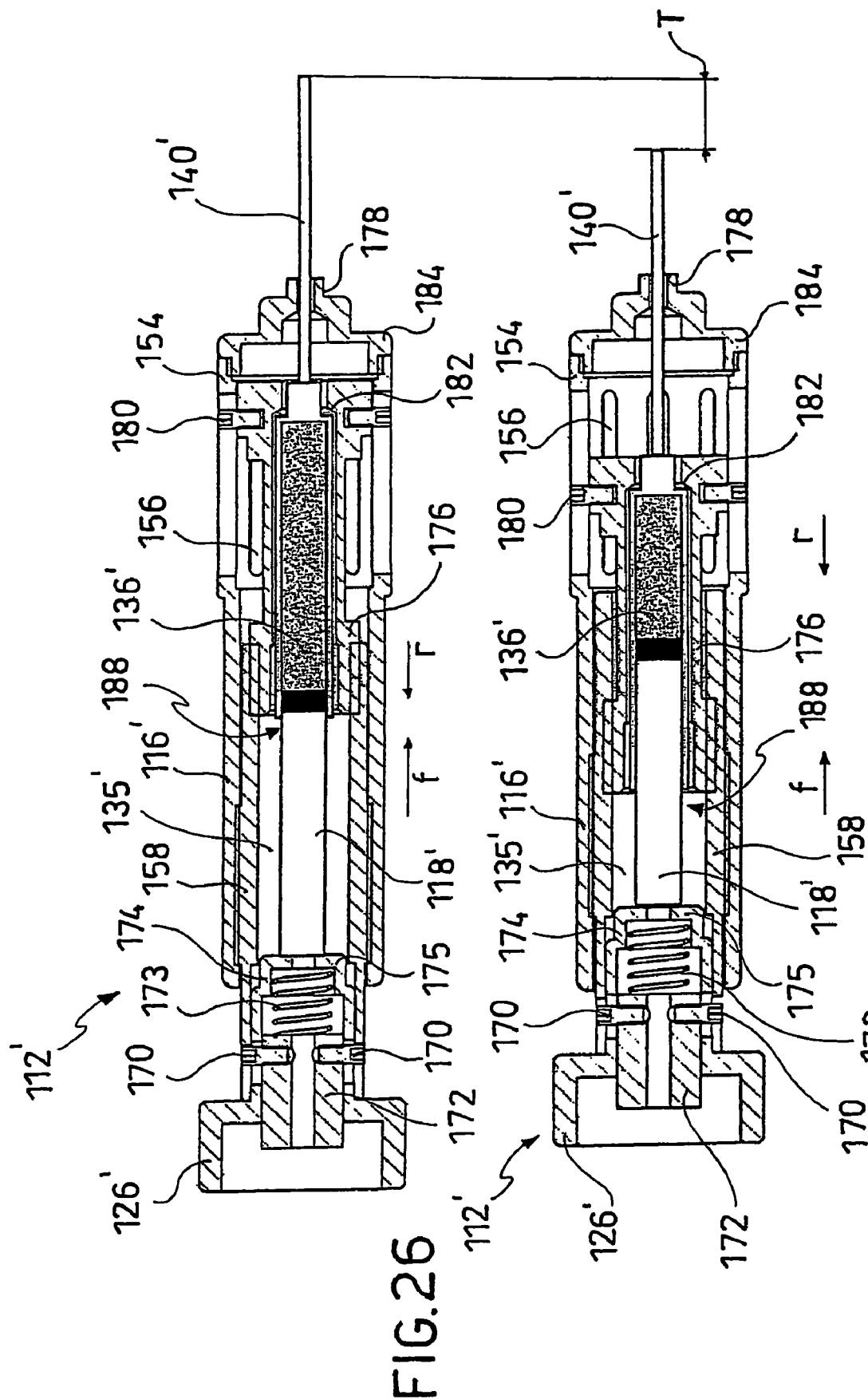

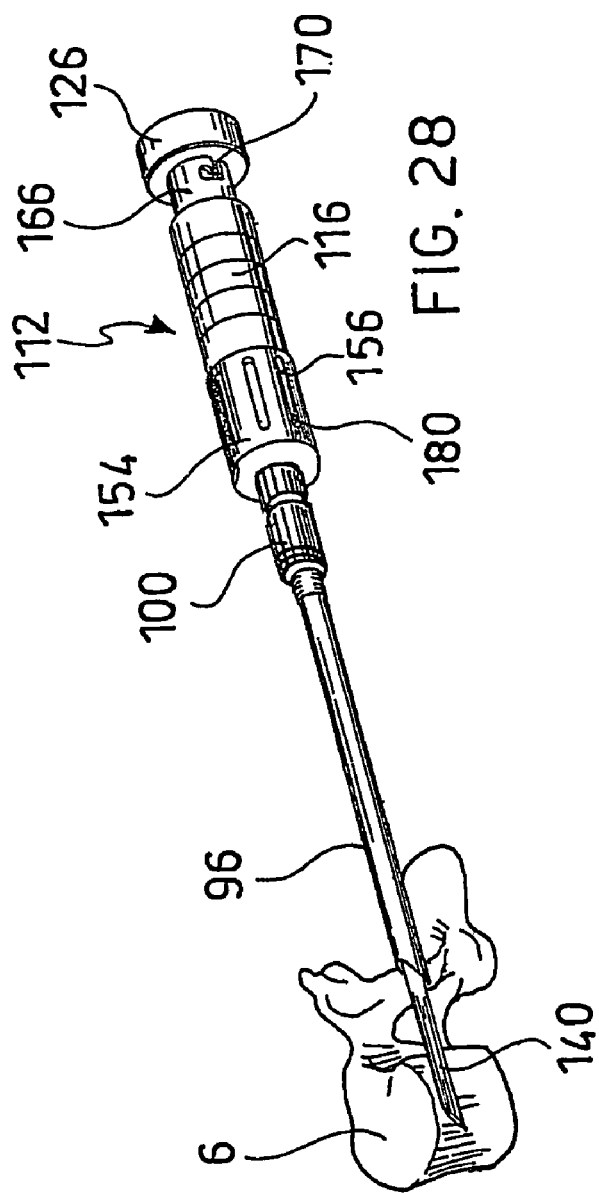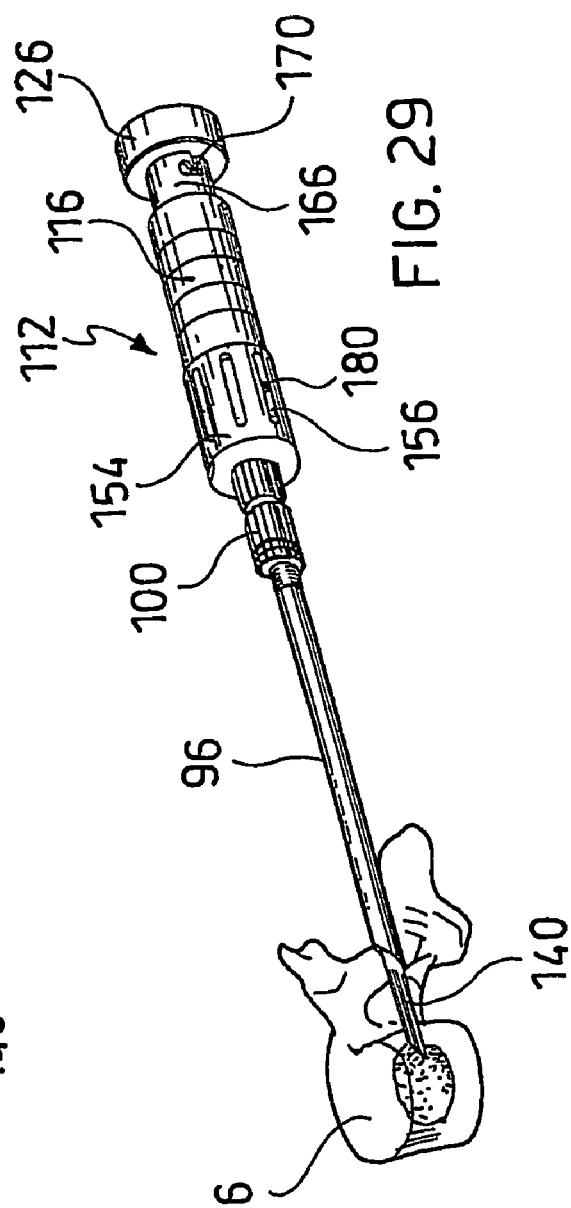

DEVICES, KIT AND METHOD FOR KYPHOPLASTY

The present invention relates to a widening device for intravertebral cavities; particularly it relates to a widening device suitable to kyphoplasty operations.

The present invention further relates to an injection device for kyphoplasty suitable to inject liquid cement in a vertebral body for the reconstruction of the same.

The present invention further relates to a kit of devices for kyphoplasty and the relevant method of use.

Widening devices for use in intravertebral cavities are known to be inserted in a relaxed configuration in a vertebral body and then widened to an expanded configuration to restore the shape of the vertebral body, thereby forming a suitable cavity therein which is subsequently filled, for example with liquid cement, bone bits or bone filler of various types.

The known wideners are not able to ensure a controlled expansion inside the vertebral body, i.e. they are not suitable to provide a volume-controlled tridimensional cavity having a desired configuration.

The provision of a cavity having a well defined size is indispensable for the reconstruction of a collapsed vertebral body for example consequently to a trauma or bone degeneration.

The problem of the present invention is to provide a widening device resolving the drawbacks mentioned with reference to the prior art.

These drawbacks and limitations are resolved by a widening device in accordance with claim 1.

Other embodiments of the widening device according to the invention are described in the subsequent claims.

Further characteristics and the advantages of the present invention will be better understood from the description below of preferred and non-limiting exemplary embodiments thereof, wherein:

FIG. 4 is a magnification of the detail IV from FIG. 1;

FIG. 5A is a sectional view of the detail IV from FIG. 1 taken along line V-V from FIG. 4;

FIG. 6 is a sectional view of the device from FIG. 1;

FIG. 7 is a magnification of the detail VII from FIG. 6;

FIG. 8 is a magnification of the detail VIII from FIG. 6;

FIG. 9 is a sectional view of FIG. 3;

FIG. 10 is a magnification of the detail X from FIG. 9;

FIG. 11 is a magnification of the detail XI from FIG. 9;

FIG. 12 is a magnification of the detail XII from FIG. 9;

FIGS. 14A-14D are perspective views of a detail from FIG. 1 in a relaxed configuration and in expanded configurations according to different embodiments, respectively;

FIGS. 15A-15D are front views of FIGS. 14A-14D, respectively;

FIG. 20 is a side view of the injection device from FIG. 18 in an initial injection step configuration;

FIG. 21 is a side view of the injection device from FIG. 18 in a final injection step configuration;

FIG. 26 is a sectional view of the device from FIG. 24, at the beginning of the injection step;

FIG. 27 is a sectional view of the device from FIG. 24, at the end of the injection step;

FIG. 28 is a perspective view of the injection device from FIG. 24 as being inserted in a vertebral body, at the beginning of the injection step;

FIG. 29 is a perspective view of the injection device from FIG. 24 inserted inside a vertebral body, at the end of the injection step;

The elements or element parts in common between the embodiments described below will be indicated with the same numerals.

Figure 1:
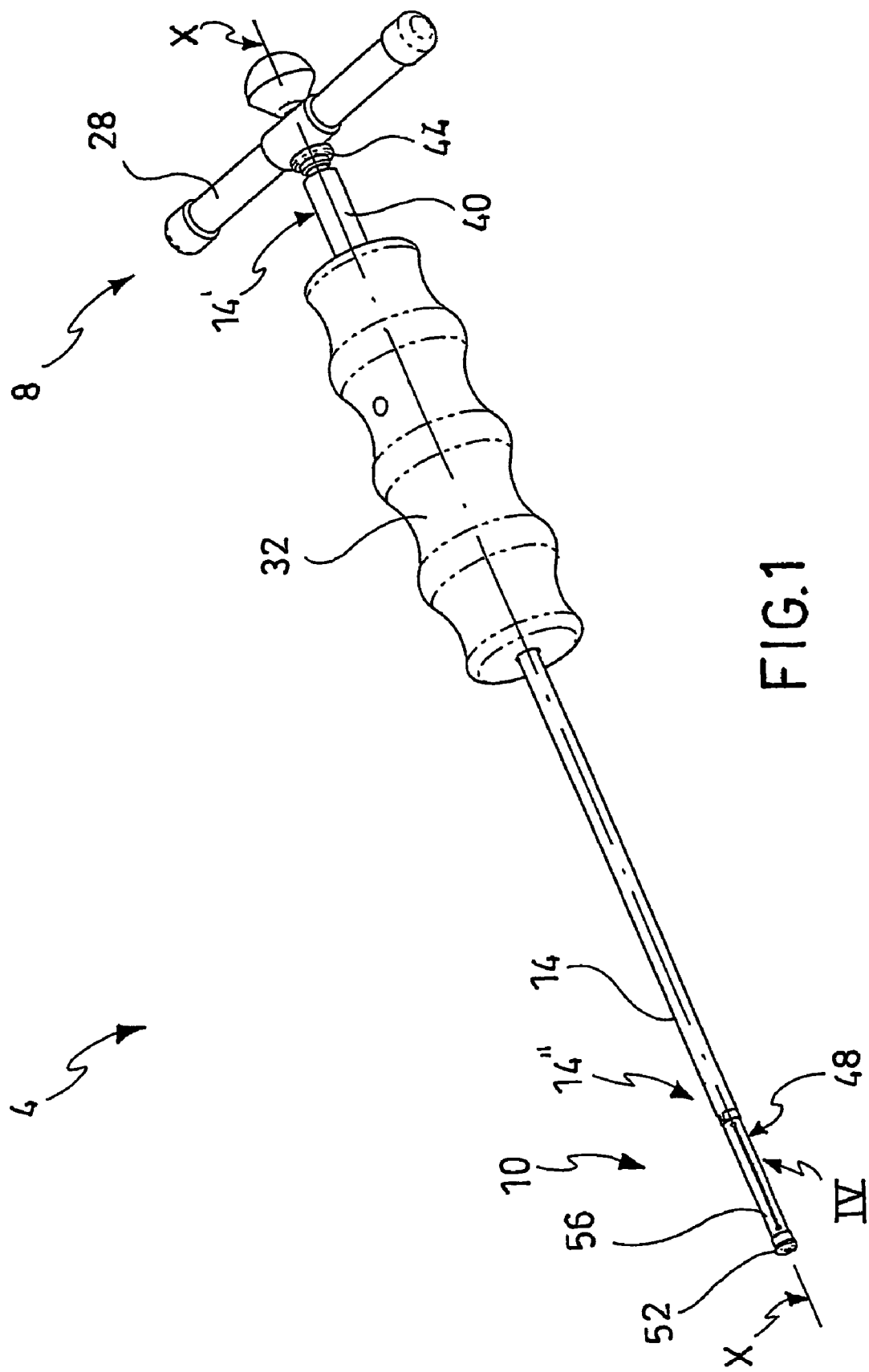
FIG. 1 is a perspective view of a widening device according to the present invention.
Figure 2:
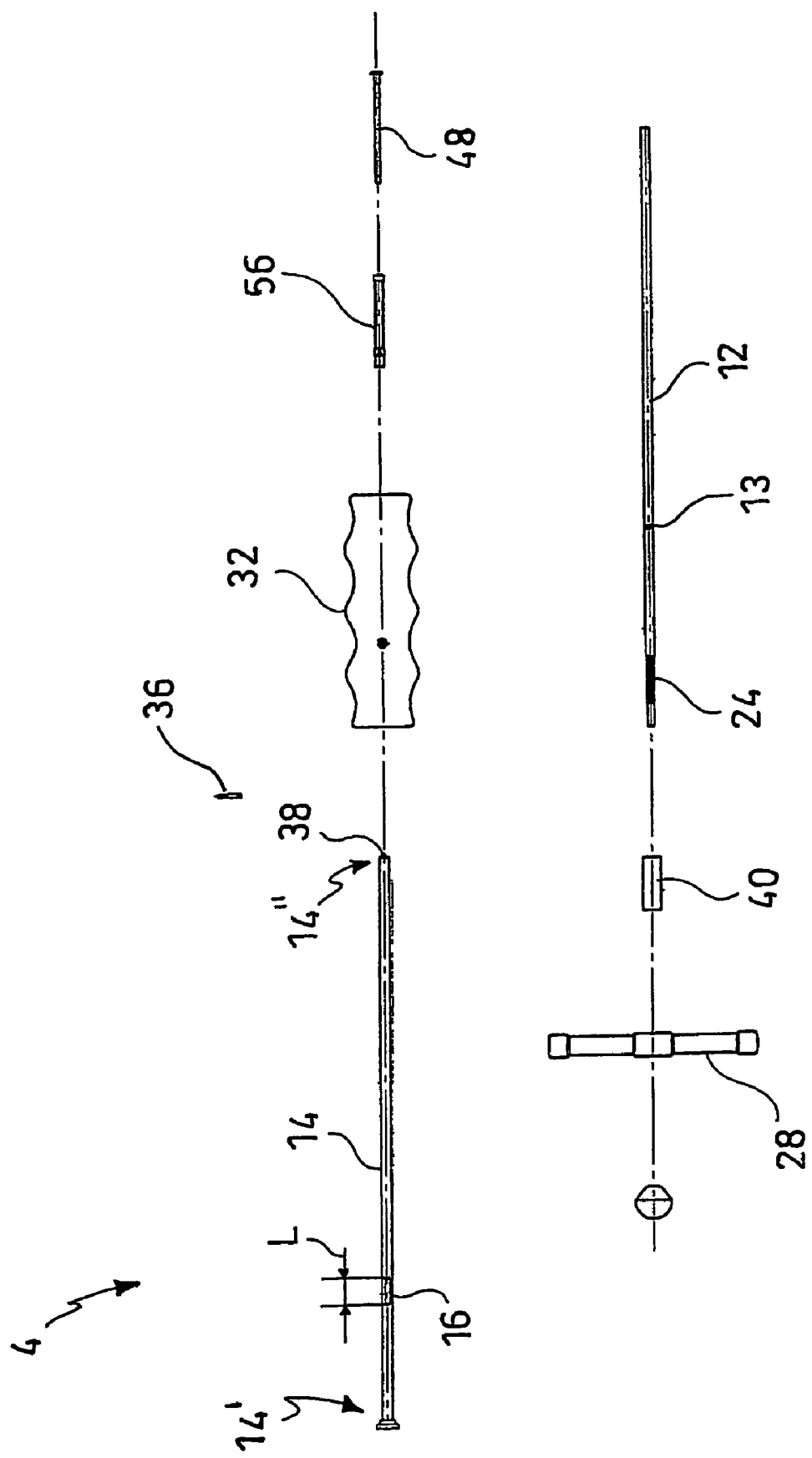
FIG. 2 is a cut-away view of the widening device from FIG. 1.
Figure 3:
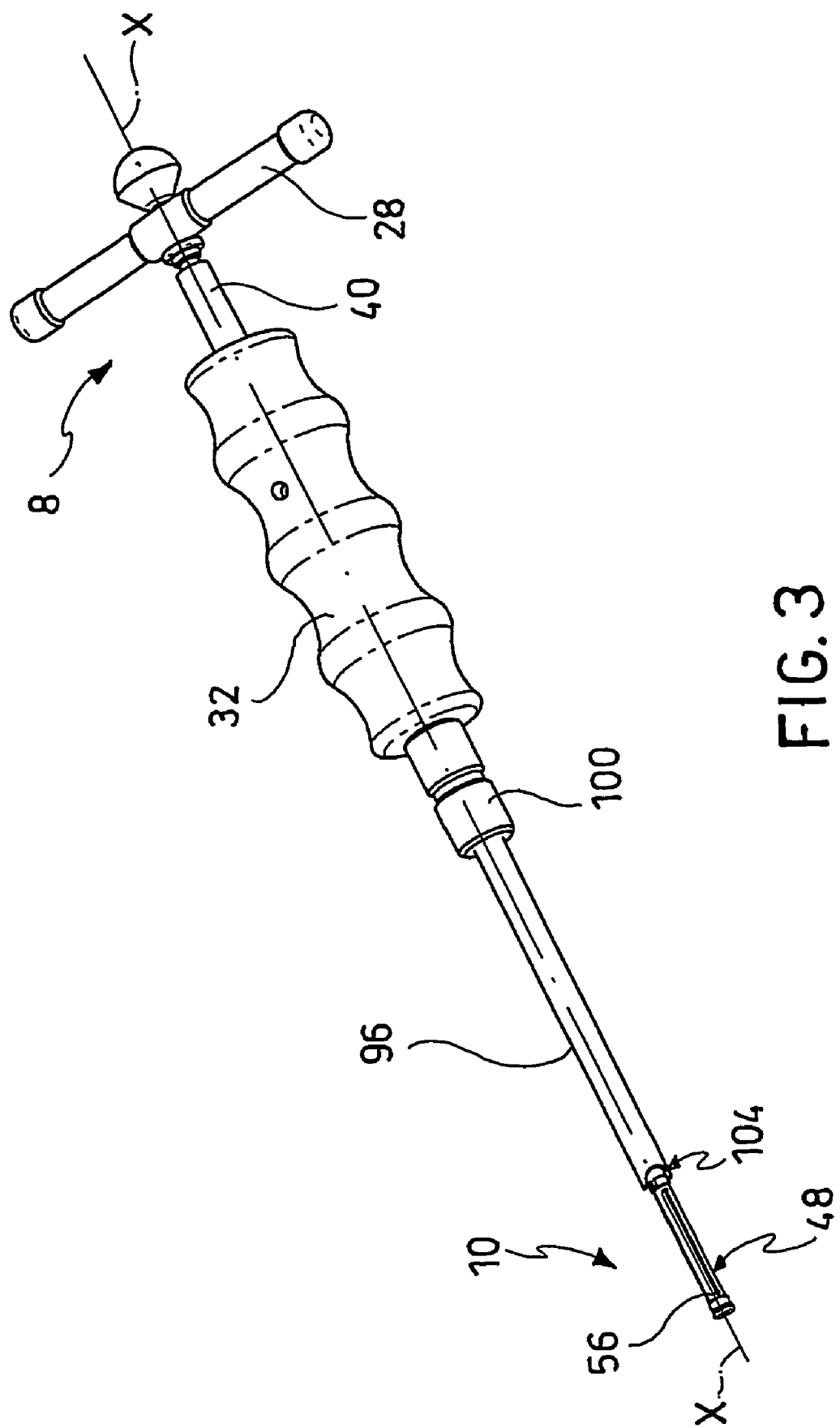
FIG. 3 is a perspective view of the widening device from FIG. 1 with the addition of accessories.

With reference to the above figures, with 4 has been generally indicated a widening device suitable to provide a cavity within a vertebral body 8.

The widening device 4 has an elongate shape as a whole and develops along an extension axis X, between a proximal end 8 and a distal end 10.

Herewith below, by axial direction will be designated a direction parallel to the extension axis X, and by radial direction will be designated a perpendicular direction to the extension axis X and incident thereto.

The widening device 4 comprises a cylindrical shank 12, extending from the proximal end 8 to the distal end 10.

The shank 12 comprises a first through hole 13 arranged on the side of the proximal end 8.

To the shank 12 there is associated a tube 14 externally and coaxially thereto, relative to axis X, such as to at least partially cover the shank 12. The tube 14 extends between a first end 14', facing the proximal end 8, and a second end 14", facing the distal end 10.

The tube 14 comprises an aperture 16 having an axial extension L, arranged on the side of first end 14'.

At the proximal end 8 the shank 12 is provided with a threaded length 24 for a knob 28 to be associated thereto according to a screw-nut type coupling.

To the shank 12 and tube 14 is further coaxially associated a sleeve 32, arranged between the distal end 10 and the proximal end 8.

The sleeve 32 comprises a pin 36 mechanically connecting the sleeve 32 with the shank 12 and the tube 14 such as to rotatably lock both of them, relative to the X axis.

The pin 36 has a smaller diameter than said extension L of aperture 16.

Particularly, in an assembly configuration, said pin 36 is inserted in the sleeve 32 such as to intercept the first hole 13 of shank 12 and aperture 16 of tube 14.

Furthermore, in an assembly configuration, the second end 14" of tube 14 comprises the distal end of shank 12 therein.

The profile of end 14" of tube 14 identifies a first strike 38.

Between the sleeve 32 and the knob 28 there is inserted a spacer 40, coaxial with the shank 12, said spacer 40 at least partially intercepting the threaded length 24.

Between the spacer 40 and the knob 28 there is inserted, coaxially with the shank 12, a stop element 44, suitable to receive the knob 28 in abutment. Preferably, the stop element 44 is one-piece with the tube 14 at the first end 14'.

The spacer 40 and the tube 14 are suitable to axially slide along the extension axis X relative to shank 12.

Particularly, the spacer 40 can axially slide relative to shank 12 for a length being almost equal to the axial distance between the end of spacer 40 facing the stop element 44 and the stop element.

The tube 14 can axially slide relative to shank 12 to the extent of the backlash present between the aperture 16 and the pin 36.

At the distal end 10, to the shank 12 there is associated a cylindrical terminal 48 which, on the opposite side to the shank 12, comprises a second strike 52, of a substantially greater diameter than the diameter of shank 12.

Preferably, the terminal 48 is removably associated to shank 12, such as by means of a threaded connection.

According to an embodiment, the terminal 48 comprises a pivot suitable to be screwed to the free end of shank 12, and the pivot head provides said first strike 38.

An elastically deformable element 56 is mounted along the extension axis X, coaxially to the terminal 48.

The elastically deformable element 56 is cylindrical and hollow as a whole and is suitable to be fitted on terminal 48.

Preferably, the elastically deformable element 56 comprises a central body 57 with a diameter d, axially defined by a first and second collar 58',58" with a diameter D greater than the diameter d of the central body 57.

The elastically deformable element 56 further comprises an inserting portion 59, connected to first collar 58' and axially extending from the opposite side to second collar 58".

The inserting portion 59 is suitable to be inserted in the inner diameter of tube 14 and extends such that, in an assembly configuration and in the relaxed configuration, between the inserting portion 59 and shank 12 an axial backlash G is identified.

Preferably, the axial backlash G is almost equal to the axial extension L of aperture 16. The axial distance between the first and second collars 58',58" is almost equal to the distance between the first and second strikes 38,52; in other words, in a relaxed configuration, the central body 57 is inserted with substantially no backlash between both strikes 38,52.

In the relaxed configuration, the elastically deformable element 56 is not subjected to axial loads and is substantially parallel to the extension axis X.

Advantageously, relative to a perpendicular plane to the extension axis X, the elastically deformable element 56 has a variable thickness along said extension axis X; in other words, the radial thickness of the elastically deformable element 56 varies advantageously along a parallel direction to said extension axis X.

The elastically deformable element 56 is preferably made of a polymeric material, an elastomer, a rubber and the like. The preferred materials to be used are characterized by a high modulus of elasticity value, such as to ensure high distraction forces and resistance to considerable loads, as well as characterized by a low ratio of the modulus of elasticity and the yield stress, such as to minimize the risk of yield due to great deformation.

Furthermore, metal, composite or polymeric materials, as well as shape-memory, metal or polymeric materials can also be used.

Preferably, the deformable element 56 comprises at least one tab 60 which, in the relaxed or undeformed configurations, extends substantially parallel to axis X.

The at least one tab 60 is formed in the elastically deformed element 56 by means of longitudinal grooves 64.

Advantageously, at ends facing the first and second collars 58',58", respectively, the grooves 64 end with slots 68, for example of a circular shape.

According to an embodiment, each tab 60 has a central portion 72 and two side portions 76', 76" being axially arranged on opposite sides to the central portion 72.

The side portions 76', 76" are in turn connected to the respective collars 58',58" through attachment portions 80', 80".

According to an embodiment, the tabs 60 have a midplane S perpendicular to the extension axis X and positioned in the middle of central portion 72; in other words, the side portions 76', 76" and the attachment portions 80', 80" have the same axial extension. According to further embodiments, the side portions 76',76" and/or the attachment portions 80',80" have different axial extensions.

According to further embodiments, the tabs 60 have only one side portion 76' or 76" and do not exhibit the midplane S, i.e. the central portion is directly connected to the respective collar 58' or 58".

Furthermore, the central body 57 can have an outer diameter varying along the longitudinal extension of the same.

Figure 5B:
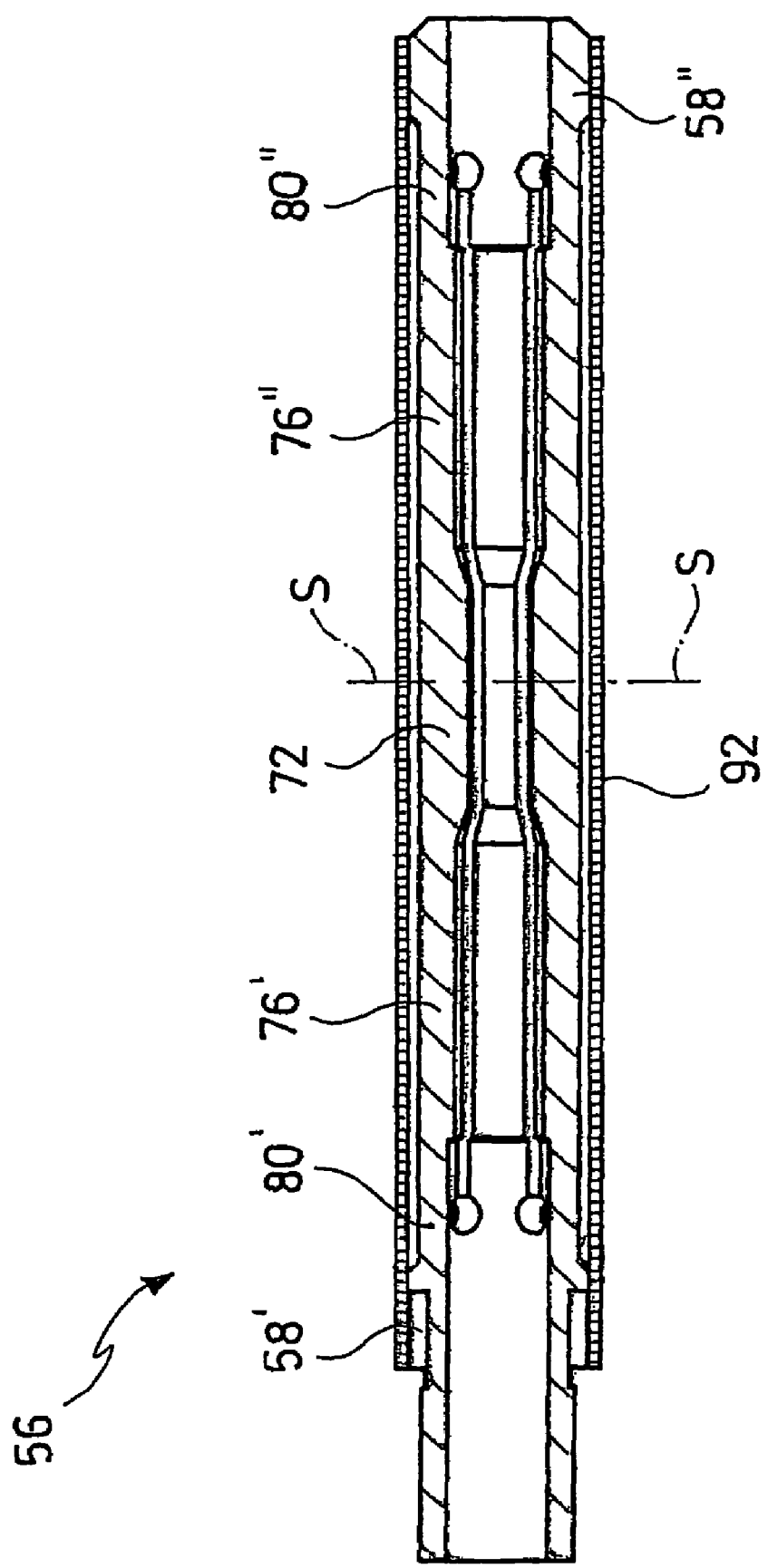
FIGS. 5B-5D show the detail from FIG. 5A comprising a sheath according to different embodiments of the invention.
Figure 5C:
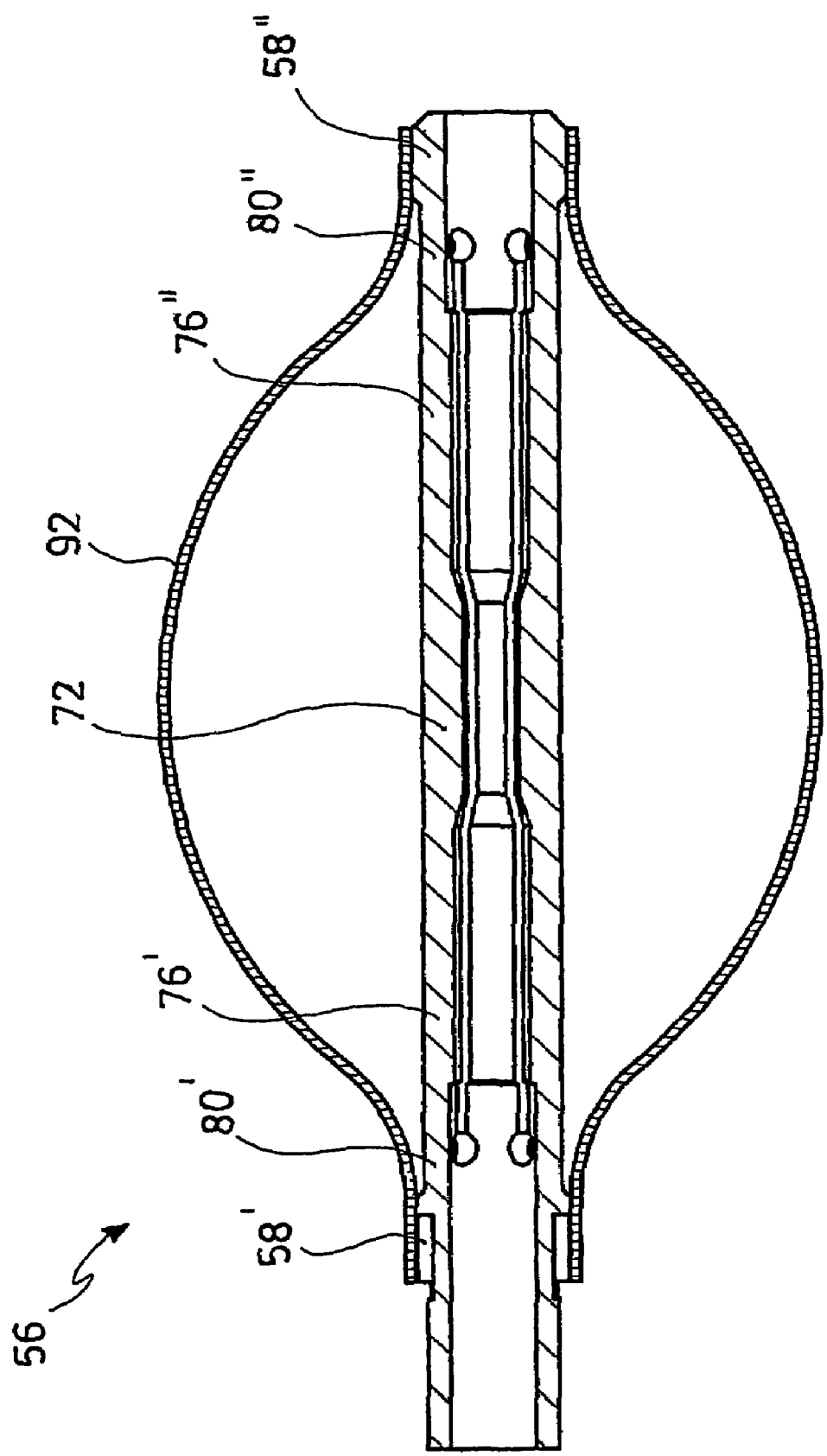

Such as for example illustrated in FIG. 5, each tab 60 advantageously has radial thicknesses varying along the extension axis X. This variation in the thicknesses can be discrete, such that the elastically deformable element 56 has marked variations in the thickness for example at the interface areas between the central portion 72 and the side portions 76',76" or between the side portions 76',76" and the attachment portions 80',80". According to a further embodiment this variation in the thicknesses is gradual and continuous, i.e. said interface areas between the central portion 72 and the side portions 76',76" or between the side portions 76',76" and the attachment portions 80',80" are suitably linked up to one another in the thicknesses thereof.

For example, at the central portion 72, the greater thickness of each tab 60 gradually decreases towards the attachment portions 80', 80".

Furthermore, each tab 60 has, relative to a perpendicular plane to the extension axis X, a section shaped like a ring sector, having a minor arch 84 facing the axis X and a major arch 88 facing outwardly.

Preferably, the elastically deformable element 56 has a plurality of tabs 60; according to some preferred embodiments, such as illustrated for example in FIGS. 14A-14D, the elastically deformable element 56 has three or four tabs symmetrically or asymmetrically arranged relative to the extension axis X.

According to an advantageous embodiment, said elastically deformable element 56 comprises a sheath 92 extending between the attachment portions 80',80" such as to wrap or cover said tabs 60.

In the relaxed configuration of the elastically deformable element 56, the sheath 92 has a substantially axial-symmetrical extension coaxial with the extension axis X. According to an embodiment, the sheath 92 has a cylindrical extension, with a substantially constant diameter, such as to at least partially adhere to tabs 60 also in a relaxed configuration. According to a further embodiment, the sheath 92 has a cylindrical extension with a varying diameter such as to adhere, in a relaxed configuration, to the elastically deformable element 56 at the collars 58',58". According to a further embodiment, the sheath 92 has an ellipsoidal extension as a whole in a relaxed configuration, having a varying diameter along the extension of said axis X, for example such as to come in contact with tabs 60 at the collars 58',58" and not at the central portion 72 of tabs 60. Furthermore, the sheath 92 can be double-lobe shaped or however have a varying section along the longitudinal extension of sheath 92, said section being taken on a perpendicular plane to axis X.

Figure 5D:
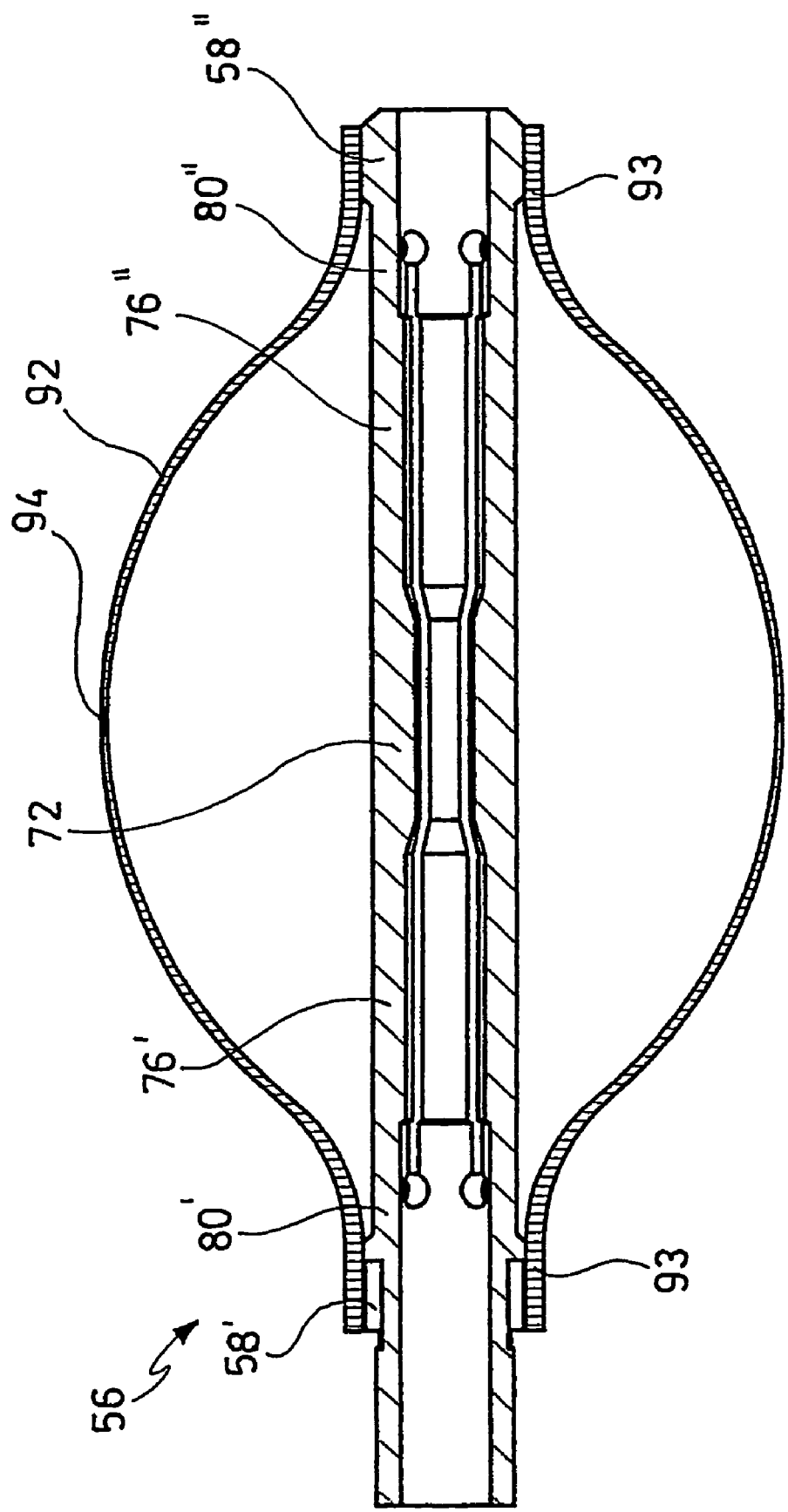
Figure 13:
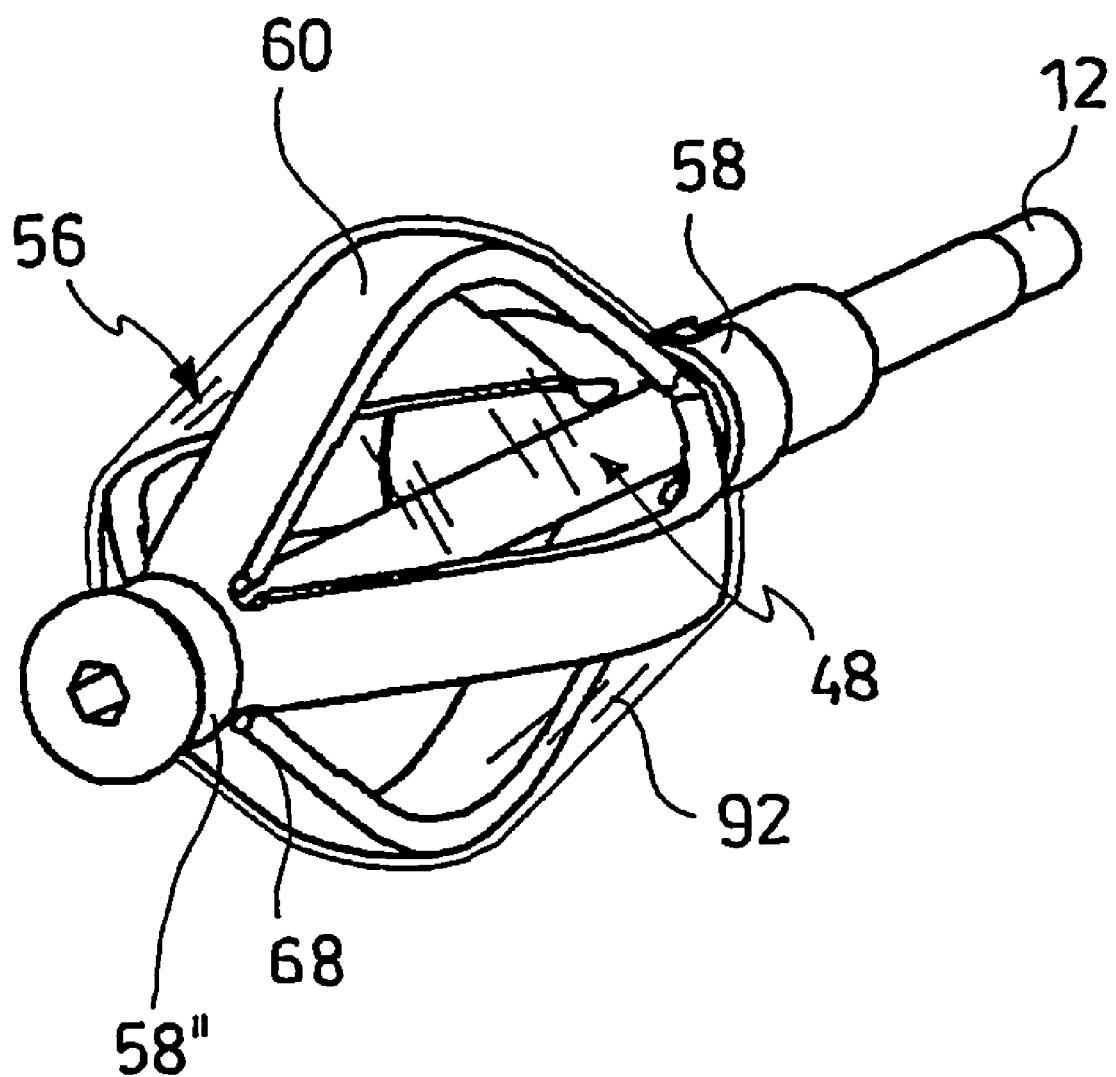
FIG. 13 is a perspective view of a detail of the device from FIG. 1 in an expanded configuration.
Figure 16:
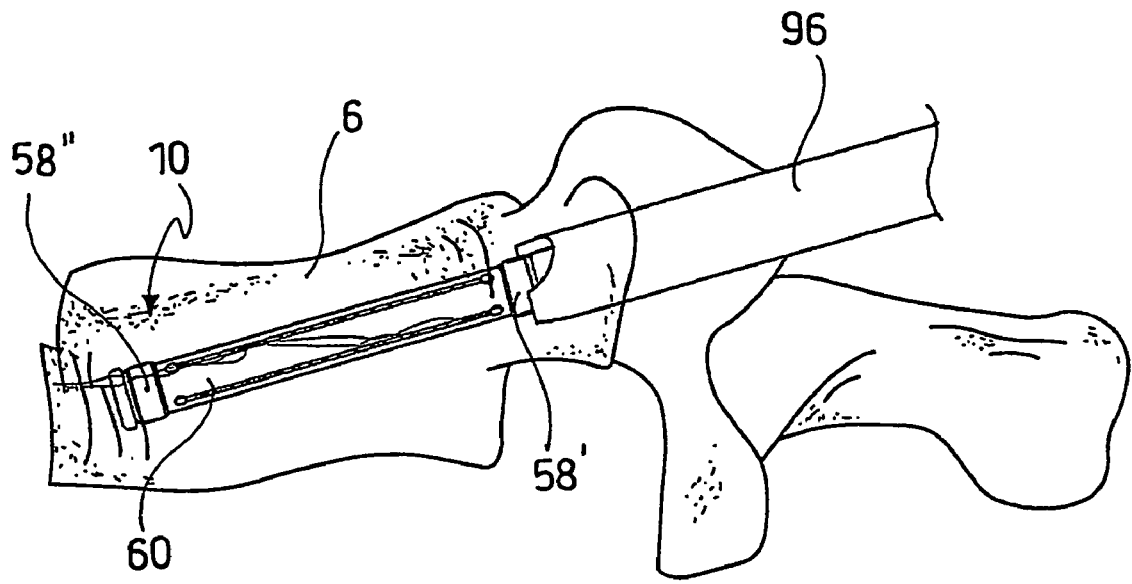
FIG. 16 is an insertion diagram of the device from FIG. 1 in a collapsed vertebral body, in a relaxed configuration.
Figure 17:
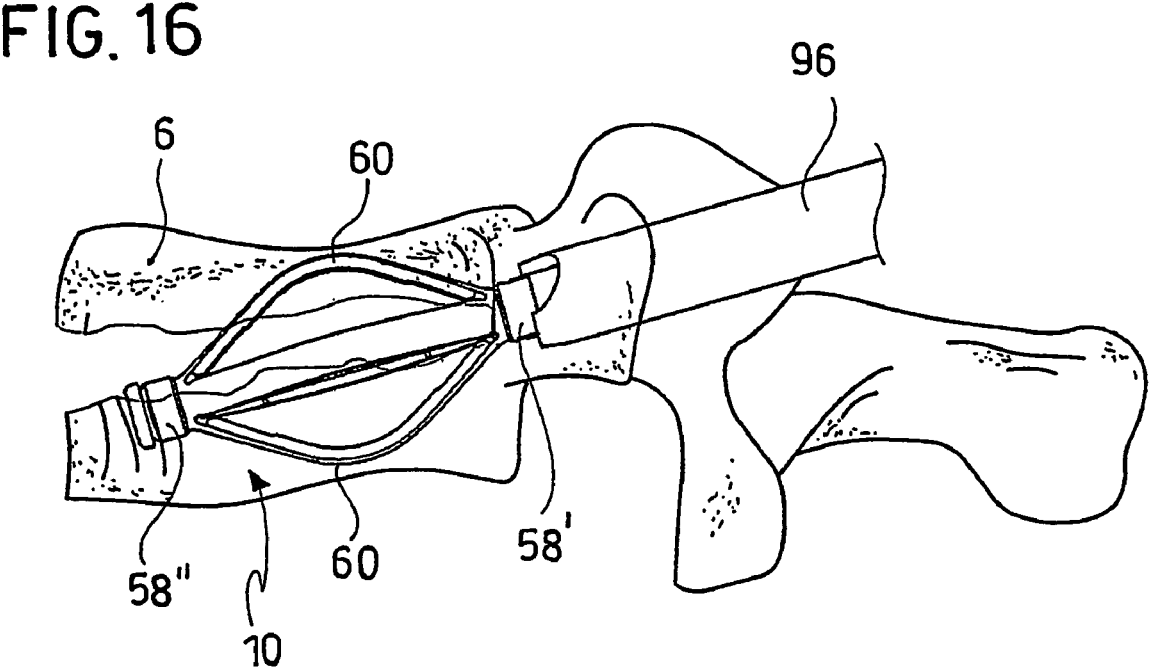
FIG. 17 is an insertion diagram of the device from FIG. 1 in a restored vertebral body, in an expanded configuration.

According to an embodiment the sheath 92 has a constant thickness along the extension thereof. According to a further embodiment, such as illustrated in FIG. 5D, the sheath 92 has a varying thickness along the extension thereof; for example the sheath 92 has a thickening 93 at the connecting portions to the elastically deformable element 56 and a thinning 94 in a portion comprised between said connecting portions and facing for example the central body 57 of tabs 60.

Preferably, the sheath 92 is made of an elastic material such as a polymer, an elastomer, a rubber, and is suitable to be matched to the tabs 60 in the deformed configuration.

According to an embodiment, the sheath 92 is associated to the elastically deformable element 56 by glueing at the first and second collars 58',58".

According to an advantageous embodiment, the widening device 4 comprises a cylindrical cannula 96 suitable to cover the tube 14 in the length comprised between the distal end 10 and sleeve 32.

Preferably, said cannula 96 is provided with a threaded bush 100 at a connecting end 106 facing the sleeve 32; the bush 100 acts as an adjusting sleeve to tailor the insertion depth of the widening device 4 inside the vertebral body 6.

Advantageously, said cannula 96 is provided with a gripping end 104, suitable to be locked within the vertebral body 6, such as to form a guide for the widening device 4 to be inserted therein, and also for the insertion of a probe to first inspect the interior of the vertebral body 6. Advantageously, the cannula 96 allows the use, i.e. the coupling with endoscopic, microscopic systems and for biopsy sampling.

Furthermore, the cannula 96 is advantageously suitable to at least partially house a cement injection device 112 to fill the intravertebral cavity with liquid cement.

The injection device 112 comprises a grip element 116 suitable to allow the grip by a user and having a pusher 118 for example of a cylindrical shape, integrally connected to the grip element 116. In an assembly configuration of the injection device 112 on the cannula 96, the pusher 118 is coaxial to the extension axis X. The grip element 116 further comprises at least one seat 120.

Figure 18:
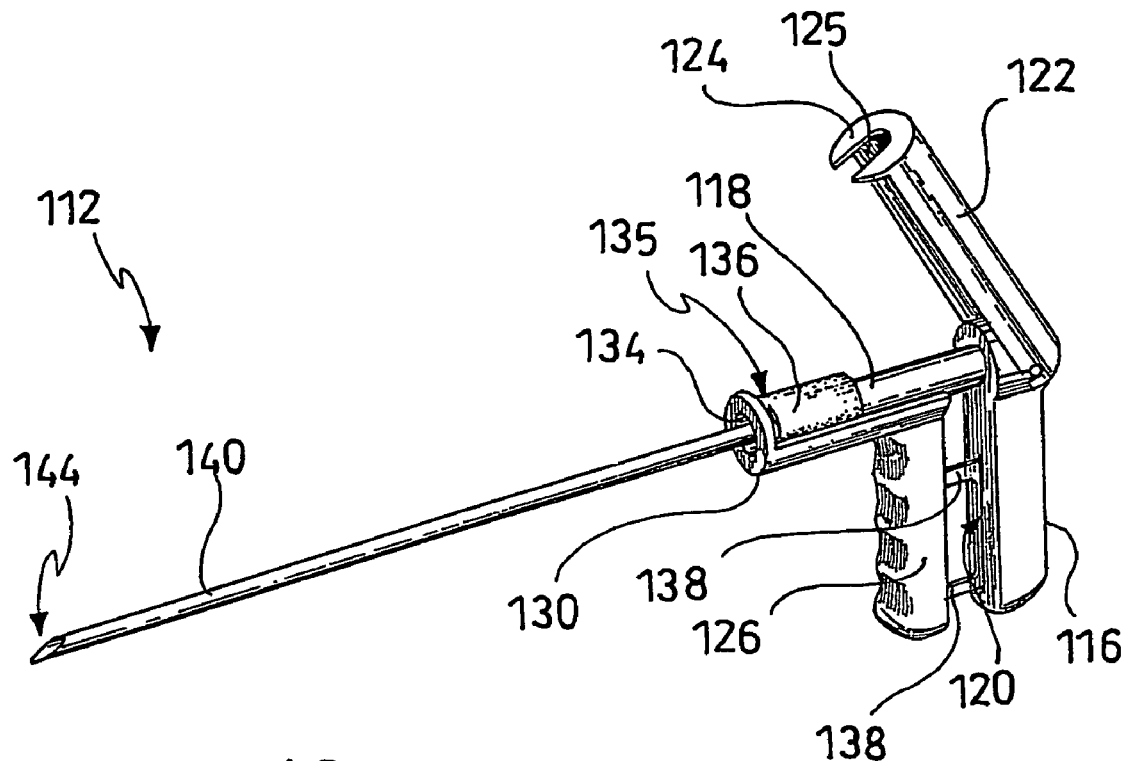
FIG. 18 is a perspective view of an injection device according to the invention, in an open configuration of the device.
Figure 19:
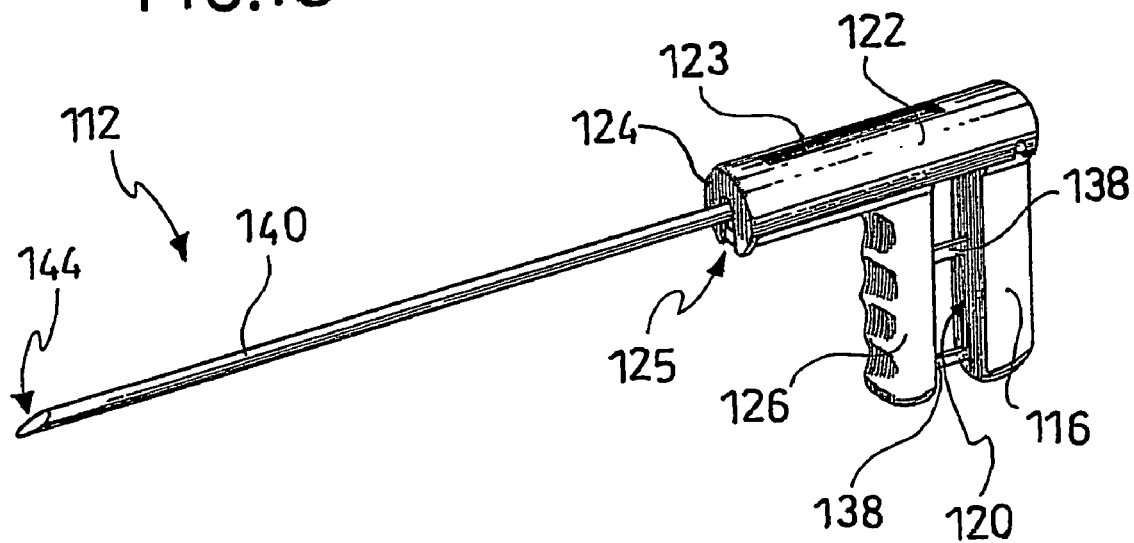
FIG. 19 is a perspective view of the injection device from FIG. 18, in a closed configuration of the device.
Figure 22:
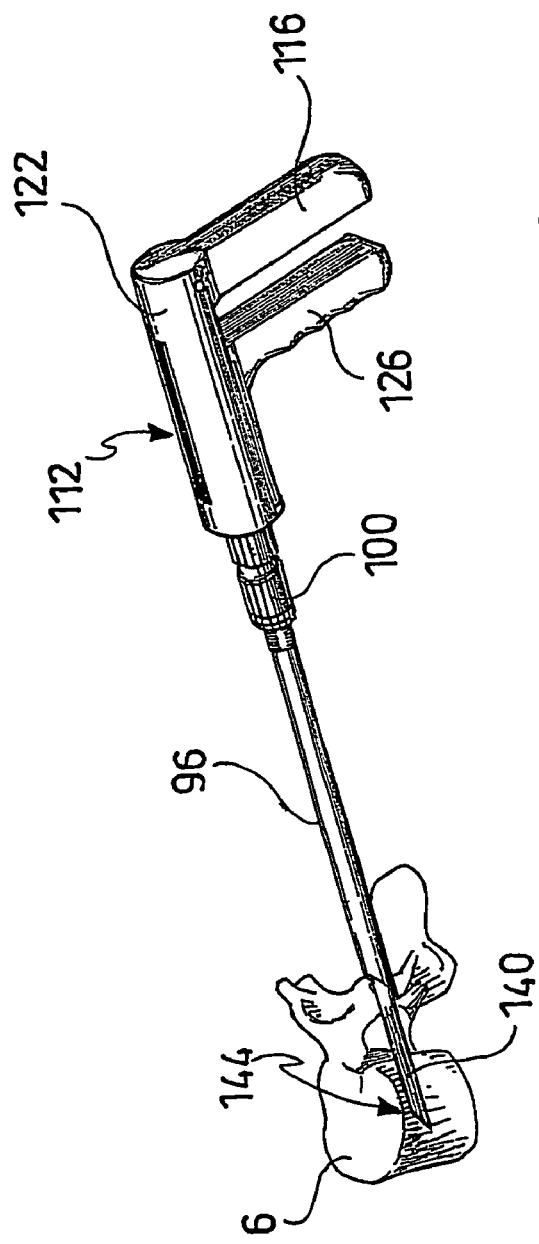
FIG. 22 is a perspective view of the injection device from FIG. 18 as being inserted in a vertebral body at the beginning of the injection step.
Figure 23:
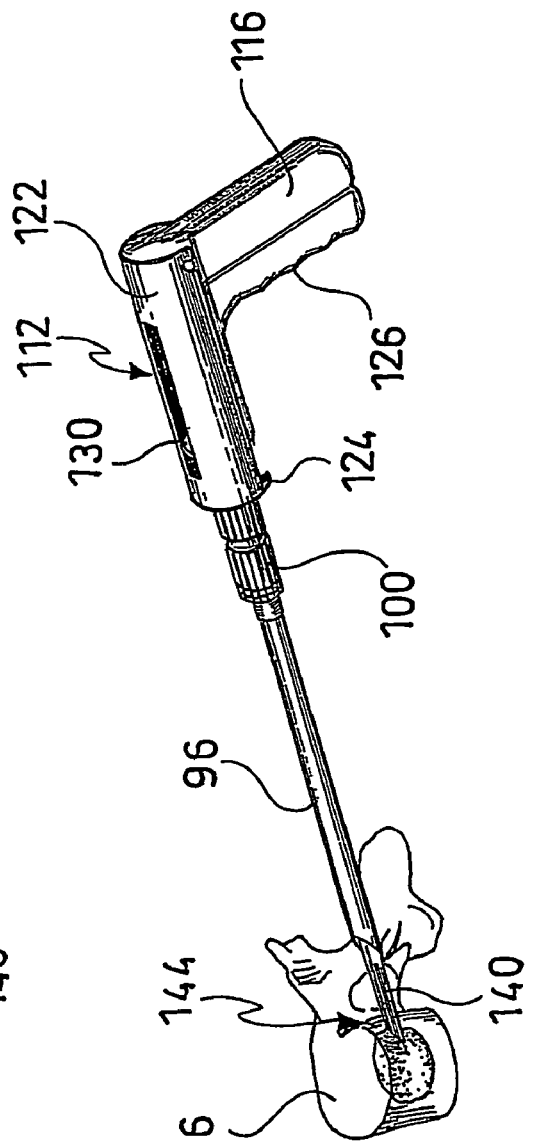
FIG. 23 is a perspective view of the injection device from FIG. 18 as being inserted in a vertebral body, at the end of the injection step.
Figure 24:
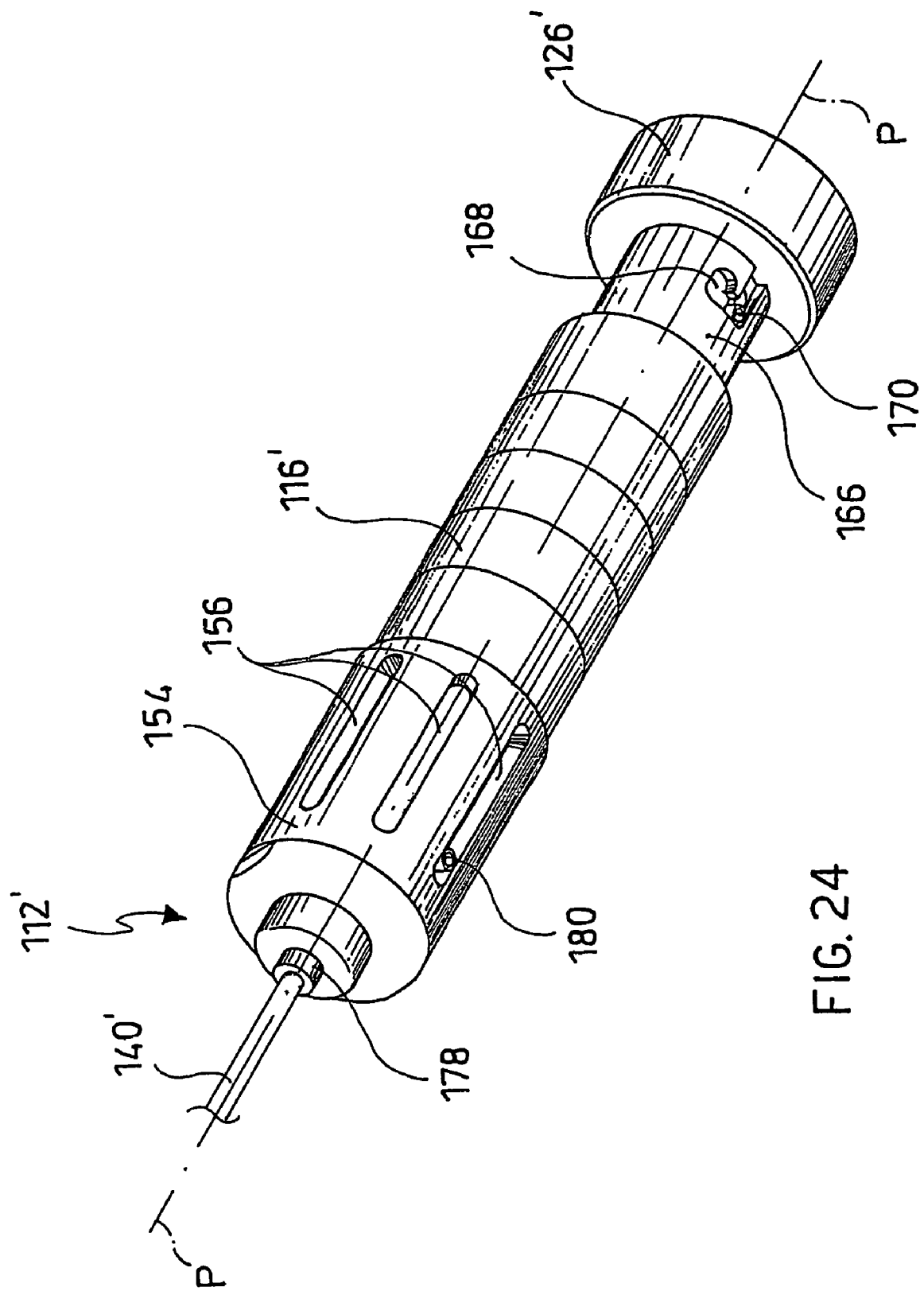
FIG. 24 is a perspective view of an injection device according to a further embodiment of the invention.
Figure 25:
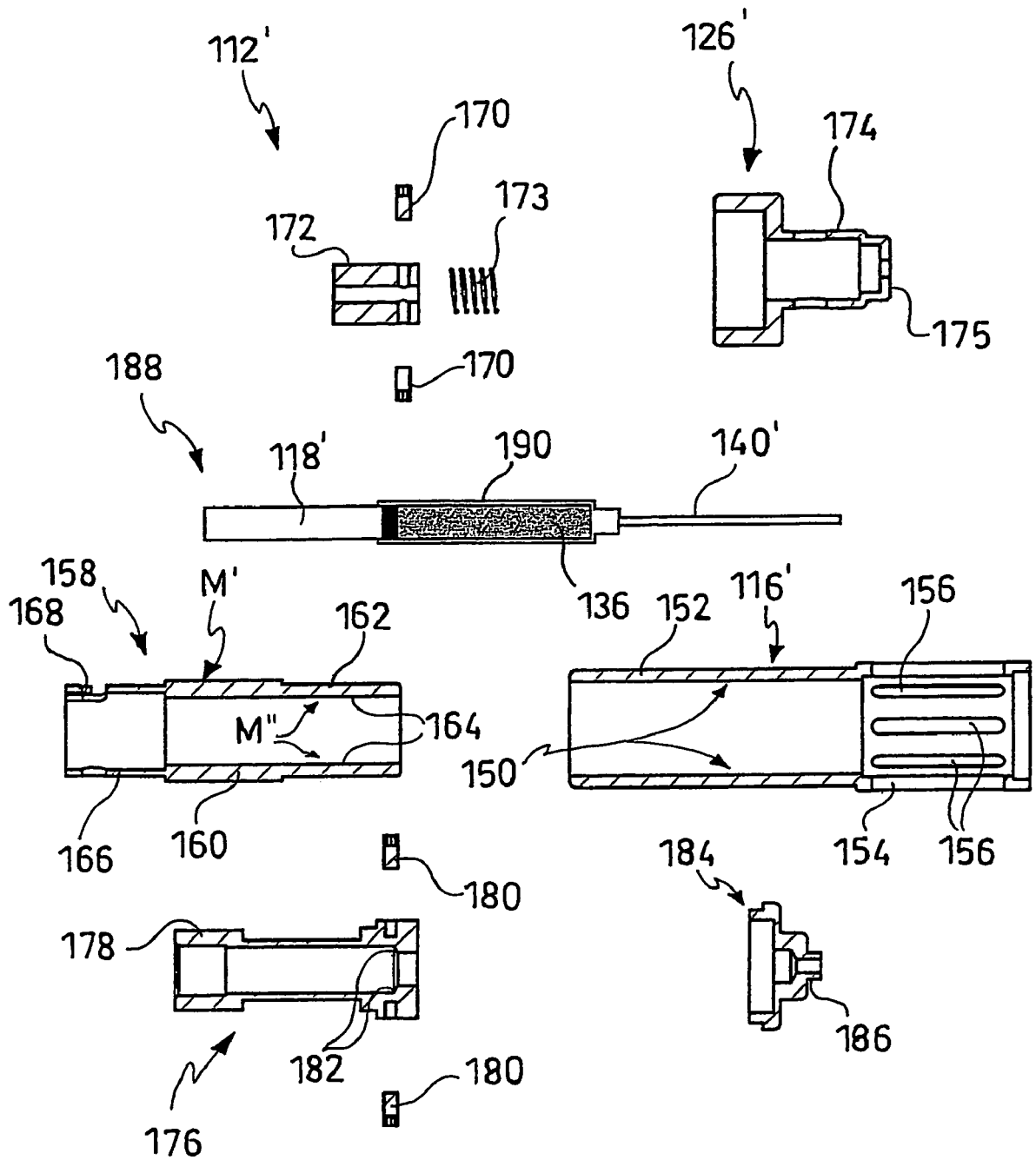
FIG. 25 is a cut-away sectional view of the device from FIG. 24.

On the grip element 116 there is hinged a lid 122, suitable to rotate from an open position, such as illustrated for example in FIG. 18, to a closed position such as illustrated for example in FIG. 19.

The lid 122 further comprises a window 123 and a corresponding graduated scale suitable to measure the relative translation between a control element 126 and the grip element 116. At an end facing the hinging end of the grip element 116 on lid 122, the lid 122 ends with a stop 124 having a notch 125.

To said grip element 116 there is associated the control element 126 mechanically connected to a plate 130, of a circular shape having a second hole 134.

The control element 126 and the grip element 116 in a closed configuration, where the stop 125 and the plate 130 directly face each other, identify a chamber 135 suitable to house a cement cartridge 136 to be injected.

Preferably, the control element 126 comprises at least one guide 138 suitable to be at least partially housed within said seat 120, such that the motion of the control element 126 relative to the grip element 116 is guided substantially along a stroke T according to a direction parallel to axis X.

A cylindrical needle 140, hollow and suitable to be housed within the cannula 96, is mechanically associated to the plate 130 through said second hole 134 such that an injection end 144 of needle 140 is fluidically connected to chamber 135.

A further embodiment of an injection device 112' will be now described, such as illustrated for example in FIGS. 24-29, wherein the elements or parts in common with the embodiment illustrated above will be indicated with the same numeral provided with primes.

The injection device 112' has a cartridge configuration as a whole, of main extension P. The injection device 112' comprises a hollow grip element 116' of a cylindrical shape suitable to be held by a user. At an inner side wall 150 the grip element 112' comprises a first threading 152 with pitch M'. Opposite to the first threading 152, relative to the main extension P, the grip element 112' comprises a flange 154 having longitudinal guides 156 arranged parallel to the main extension P.

A first cylindrical and hollow ring nut 158 is suitable to mesh with said first threading 152 at a first control portion 160 such as to be coaxially mounted to the grip element 116' and internally thereto.

The first ring nut 158, opposite to the first control portion 160, comprises a second control portion 162 provided at an inner part, i.e. towards the extension axis P, with an inner threading of pitch M", other than said pitch M'. Advantageously, pitch M" of second threading 164 is greater than pitch M' of first threading 152; preferably pitch M" is about twice the pitch M'.

The first ring nut 158, opposite to the second threading 164, comprises a neck 166 provided with a notch 168. At the neck 166, to the first ring nut 158 there is associated a control element 126' preferably in the form of a hollow knob. Particularly, the control element 126' is removably fastened to the neck 166, through a bayonet-type arrangement, by means of at least one stake 170 suitable to be locked within said notch 168. Between the control element 126' and the neck 166 there is interposed a barrel 172 for the at least one stake 170 to be mounted thereto; the barrel 172 is provided with a spring 173 such as to force said stake against the corresponding notch 168.

The control element 126' comprises a bell 174 suitable to house said barrel 172 and suitable to be at least partially inserted in the first ring nut 158 from the neck 166. The bell 174 axially ends with a stop surface 175, such as of a disc-shape type.

In an assembly configuration, the control element 126', the barrel 172 and the first ring nut 158 are preferably rotatably integral to one another.

To the grip element 116', opposite to the first threading 152, there is associated a second ring nut 176 having an outwardly threaded portion 178 suitable to mesh with the second threading 164. Opposite to the outwardly threaded portion 178, along extension P, the second ring nut 176 comprises at least one pivot 180 suitable to be housed within said longitudinal guides 156, such as to longitudinally slide therealong; furthermore, the second ring nut 176 comprises an abutment surface 182 of a circular ring shape. To the second ring nut 176 is further associated a cylindrical plug 184, arranged at the opposite end of the control element 126', and preferably comprising a threaded ring 186 suitable to be screwed on the threaded bush 100.

In an assembly configuration, the first ring nut 158 and the second ring nut 176 are coaxially and partially mounted within the grip element 116' such as to define a substantially cylindrical chamber 135'.

The injection device 112' is suitable to contain within said chamber 135' a substantially cylindrical syringe 188 comprising a syringe body 190 enclosing a cement cartridge 136' to be injected, a pusher 118' being associated thereto, which is suitable to compress said cement cartridge 136'. The cement cartridge 136', opposite to the pusher 118', is fluidically connected to a needle 140' and according to an embodiment, the syringe body 190 is one-piece with the needle 140'.

Figure 30:
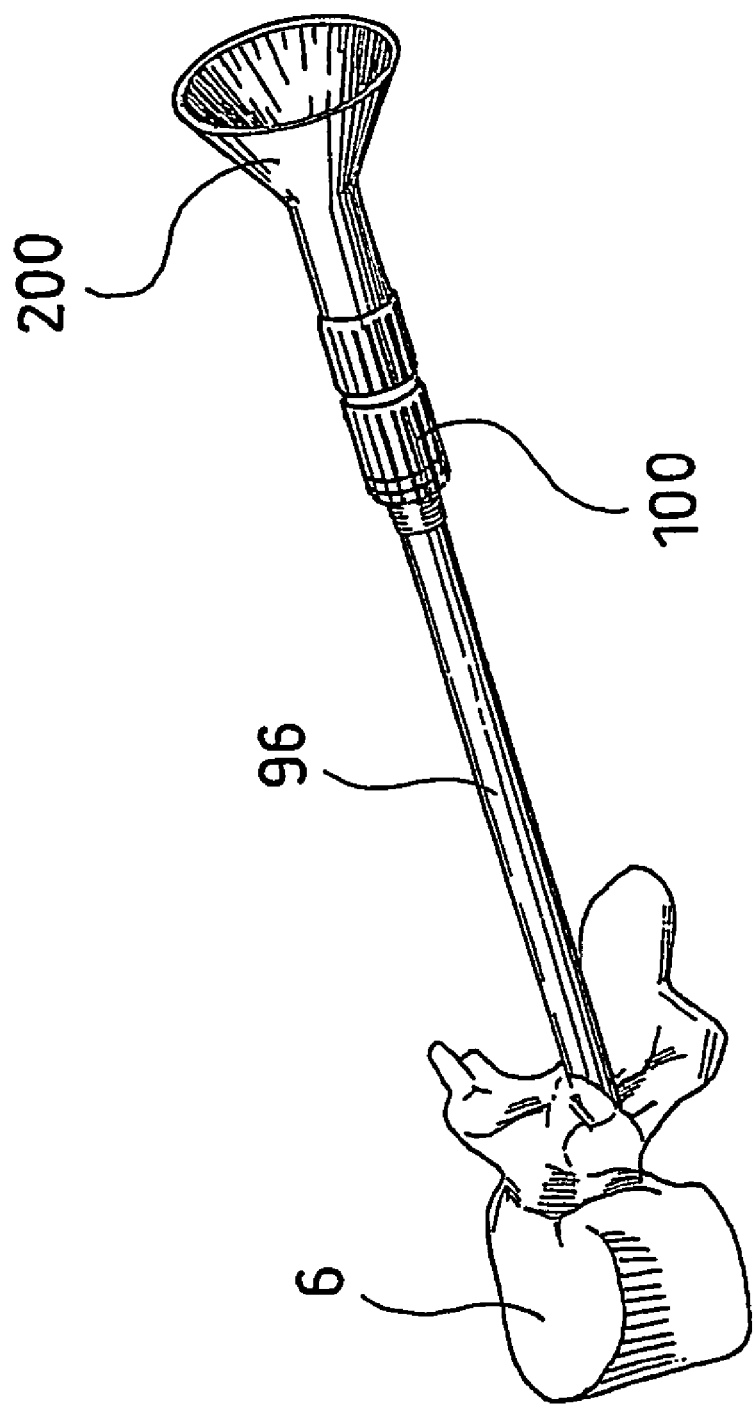
FIG. 30 is a perspective view of a device for the insertion either of bone bits or bone filler in a vertebral body.

As illustrated for example in FIG. 30, the cannula 96 is further suitable to be connected to a funnel 200, at the proximal end. Said funnel 200 is suitable to allow bone bits, i.e. bone fragments, such as taken from the iliac crest or generally bone substitute to be inserted therein.

Furthermore, the cannula 96 allows a rammer, i.e. an elongate cylindrical body having a rounded end, suitable to compact the bone bits or the bone substitute inserted therein, to be inserted within the intravertebral cavity by means of the cannula 96.

The operation of the widening device according to the invention will be now described.

At first, the cortical and sponge tissues of the vertebral body 6 are pierced with a punch such as to enable the cannula 96 to be firmly fixed to the vertebral body 6.

An endoscope may be firstly inserted in said cannula 96 to inspect the interior of the vertebral body.

The cannula 96 can then house the widening device 4 therein.

In order to properly tailor the insertion depth of the widening device 4 the above threaded bush 100 can be used to act as the adjustment sleeve.

The elastically deformable element can be then expanded 56.

Particularly, the knob 28 can be rotated on the threaded length 24 of shank 12, by holding the sleeve 32 at the same time, such as to cause the shank 12 to be tensioned, which is rotatably locked by the pin 36 of sleeve 32.

The shank 12 translatably drags the terminal 48 and the elastically deformable element 56 which in turn pushes the first strike 38 of tube 14. The tube 14 translates at first towards the proximal end until completely recovering the backlash between the pin 36 and the aperture 16.

The rotation of knob 28 generates the compression of the elastically deformable element 56 between the first and second strike 38,52. Following said compression the tabs 60, subjected to a compression load, tend to inflect outwardly, thereby taking an expanded or deflected configuration, such as arch-shaped.

While being bent, the tabs 60 are advantageously encircled by the sheath 92 filling the gaps or grooves 64 between the tabs 60.

Once the desired size has been obtained for the intravertebral cavity the widening device 4 can be disabled.

By rotating the knob 28 to the opposite direction the elastically deformable element 56 is unloaded and tends to return in the undeformed or relaxed configuration due to the elasticity of tabs 60. The sheath 92 until being stressed by the action of the tabs 60, cooperates to the passage from the deformed configuration to the undeformed configuration.

Therefore, the passage from the deformed configuration to the undeformed or relaxed configuration does not take place by applying another external force, but by removing the initial deformation force, i.e. by unloading the shank 12 and the elastically deformable element 56 accordingly.

The axial backlash between the pin 36 and the aperture 16 on tube 14 ensures that, once the knob 28 has been completely unscrewed, the tabs 60 can completely stretch without having compression loaded residues.

On the contrary, there would be the risk for the elastically deformable element 56 to be locked inside the vertebral body 6 or inside the cannula 96.

The widening device 4 can be then extracted and the injection device 112,112' or the funnel 200 can be subsequently inserted to fill the intravertebral cavity with liquid cement or bone bits, respectively.

The operation of the injection device 112 according to an embodiment will be now described.

Particularly, once the cartridge 136 has been inserted in chamber 135, and the lid 122 has been closed, one holds the grip element 116 and presses the control element 126, such as to approach i.e. move the control element 126 backward towards the grip element 116. The cartridge 136 is compressed between the plate 130 translatably dragged by the grip element 116 and the pusher 118. The cement contained in the cartridge 136 tends to flow inside the needle 140 and to exit through the injection end 144 of the same.

During the backward motion of the control element 126, the same drags the needle 140 which tends to move backwards while the cement is being injected. Consequently, the injection end 144 moves backward during the injection step, by a stroke T equal to the translation stroke of the control element 126. The amount of cement to be injected can be controlled by directly reading the translation of needle 140 with the aid of a graduated scale on window 123 of lid 122.

The operation of the injection device 112' will be now described according to a further embodiment of the invention.

To assemble the syringe 188 within the injection device 112', the control element 126' is first extracted by disengaging the stake 170 from notch 168 of neck 166, and the barrel 172 is removed to gain access to chamber 135'.

Thereafter, the syringe 188 provided with needle 140' is inserted in the chamber 135' such as to bring the cement cartridge 136' in abutment against the abutment surface 182 of second ring nut 176. The control element 126' is then reassembled such as to bring the end surface 175 of bell 174 in contact with the pusher 118'. In other words, following the assembly of syringe 188 to the injection device 112', syringe 188 is housed coaxially to the injection device 112' as well as axially constrained from opposite sides, i.e. between the control element 126' and the second ring nut 176.

Particularly, following the assembly, the pusher 118' of syringe 188 is in abutment against the stop surface 175 of the control element 126', such as to prevent the pusher 118' to move backwards according to a backward direction r; whereas the syringe body 190 abuts against the abutment surface 182 of second ring nut 176, such that the syringe body 190 cannot be moved according to a forward motion relative to a forward direction f opposite to said backward direction r.

The outwardly threaded portion 178 is first engaged on bush 100 such as to house the needle 140' of injection device 112' within the cannula 96 and form a fluidical connection between the cement cartridge 136, the injection end 144 and the cavity of the vertebral body 6.

To perform the injection, one holds the grip element 116' and rotates the control element 126' such as to rotatably drag the first ring nut 158; particularly the first ring nut 158, by screwing on the grip element 116', moves forward, i.e. it translates towards needle 140', according to the forward direction f. The second ring nut 176 meshes in turn with the grip element 116' and, since it cannot rotate relative to the grip element 116' due to the coupling between pivots 180 and longitudinal guides 156 of flange 154, it translates away from needle 140', according to the backward direction r opposite to said forward direction f. Therefore, following the rotation of the control element 126', the first and second ring nuts 158, 176 translate along extension P in opposite directions f,r thus approaching each other respectively.

The abutment surface 182 of second ring nut 176 when being translating urges the cement cartridge 136 which is compressed between the syringe body 190 in abutment against the abutment surface 182 and pusher 118', which cannot move backward according to backward direction r due to the stop surface 175. The syringe body 190 moves backward together with the abutment surface 182 of second ring nut 176 and drags the needle 140' in its backward motion along the backward direction r. Consequently, following the rotation of the control element 126', needle 140', and particularly the injection end 144 of needle 140', moves backward by a stroke T according to the backward direction r.

Furthermore, while screwing and moving forward within the grip element 116', the first ring nut 158 translatably drags the control element 126' towards the second ring nut 176. Therefore, the stop surface 175 of the control element 126' urges in turn the pusher 118' of syringe 188 according to the forward direction f and further compresses the cement cartridge 136'. Following this compression the cement tends to exit through the injection end 144 of needle 140' and from the latter to the inside of the intravertebral cavity. The pivots 180 slide in the longitudinal guides 156 and by being visible from the outside of the injection device 112', also provide a visual indication of the feeding state of the injection, i.e. the amount of cement being injected. Preferably, near the longitudinal guides 156, there is provided, for example, a graduated scale to give an indication of the amount of cement being injected.

Advantageously, by dismounting the control element 126' during any cement injection step, the cement capsule 136' stops being subjected to compression and the cement flow through needle 140' is stopped.

As may be appreciated from what has been stated above, the widening device allows to overcome the drawbacks of the prior art widening devices.

Particularly, the widening device according to the invention allows to provide a cavity within a vertebral body in a controlled manner, i.e. by providing predetermined expansion configurations which can be adjusted according to different types of vertebral bodies and different surgical indications.

In other words, the widening device ensures an active expansion, by generating a cavity of a defined shape without being subjected to deformations by the bone tissue of the vertebral body, the mechanical characteristics of which are typically not isotropic and omogeneous.

The covering sheath, by filling the grooves comprised between the tabs, ensures continuity to the deformable element thereby preventing the individual tabs from getting entangled within the vertebral body tissue, thereby allowing the deformed configuration to return to the relaxed configuration.

Advantageously, the presence of the sheath covering the tabs prevents any inclusion of bone material within the elastically deformable element, which case may hinder the tab closing motion, i.e. their return to the undeformed configuration.

The particular varying-thickness configuration along the tabs, allows to provide greater thicknesses in the tab areas subjected to greater loads and lower thicknesses in the areas where, following the deformation, great bending is desired without yielding the material. In fact, any yield may hinder the elastic return of the deformable portion from the deformed configuration to the relaxed configuration.

In fact, the return from the deformed configuration to the relaxed configuration takes place due to the elastic return of the material following the removal of the axial force which had caused the deformation, i.e. without applying another external force.

This elastic return is favoured by the elastic action provided by the sheath which tends to cause both tabs to approach each other, thereby bringing them back to the undeformed configuration.

By providing the deformable element as one-piece, the resistance of the tabs to high work load is ensured. Particularly, the presence of the slots to the tab ends prevents the risk that any crack may propagate.

The tabs are therefore beams fitted to the ends, which when subjected to compression, instabilize and inflect outwardly, i.e. away from the extension X axis.

This arrangement provides a particular stiffness to the deformable portion and allows to vary the stiffness of the tabs by acting on the variation of thicknesses.

The backward motion of the needle during the cement injection ensures an optimum filling of the intravertebral cavity because the injection end moves gradually and automatically backward as the cavity is being filled. A uniform and omogeneous distribution of the cement being injected in the bone cavity is thereby ensured. Furthermore, due to the backward motion of the needle, overpressures in the vertebral body are prevented which may give origin to leakages of cement dangerous for the spinal marrow.

The configuration of the cannula provided with a tailored bush allows to associate different devices to this cannula for a kyphoplasty operation after only one access port has been made in the vertebral cortical area and only one cannula has been inserted as the guide member. The bush allows to change the axial position of each of the devices being inserted, particularly the insertion depth of the distal end of the widening device and the needle injection end.

Those skilled in the art, aiming at satisfying contingent and specific requirements, will be able to carry out a number of modifications and variants to the above kyphoplasty devices, which are all contemplated within the scope of the invention such as defined by the claims below.

The invention claimed is:

1. Intravertebral widening device for kyphoplasty extending from a proximal end to a distal end along an extension axis, said distal end comprising an elastically deformable element, suitable to pass from a relaxed configuration for the positioning of the distal end within a vertebral body to a deformed configuration to form a cavity within said vertebral body, wherein said elastically deformable element comprises at least one tab having, along its longitudinal extension, a thickness, as measured relative to a radial direction incident to said extension axis and contained in a perpendicular plane to said extension axis, variable along the axis such as to vary the stiffness of at least one tab along the extension thereof, wherein said at least one tab comprises a central portion and two side portions relative to said axis, opposite to said central portion, wherein said central portion has a radial thickness decreasing towards the side portions.

2. Intravertebral widening device for kyphoplasty according to claim 1, comprising, at the distal end, first and second strikes suitable to define and compress said elastically deformable element, for passing from the undeformed configuration to the deformed configuration.

3. Intravertebral widening device for kyphoplasty according to claim 2, wherein the elastically deformable element comprises a central body having a central body diameter and axially defined from first and second collars having a diameter greater than the diameter of the central body.

4. Intravertebral widening device for kyphoplasty according to claim 3, wherein said first and second collars mechanically connect the axial ends of the tabs.

5. Intravertebral widening device for kyphoplasty according to claim 4, wherein said first and second collars are one-piece with the axial ends of the tabs.

6. Intravertebral widening device for kyphoplasty according to claim 1, comprising a plurality of tabs separated from one another by means of grooves.

7. Intravertebral widening device for kyphoplasty according to claim 6, wherein said grooves comprise slots at axial ends of the tabs.

8. Intravertebral widening device for kyphoplasty according to claim 6, wherein said tabs are arranged in an axial-symmetrical manner relative to said extension axis.

9. Intravertebral widening device for kyphoplasty according to claim 6, wherein said tabs are arranged in an asymmetrical manner relative to said extension axis.

10. Intravertebral widening device for kyphoplasty according to claim 1, wherein a sheath suitable to cover said tabs is mechanically associated to said elastically deformable portion.

11. Intravertebral widening device for kyphoplasty according to claim 10, wherein said sheath is glued to said elastically deformable element.

12. Intravertebral widening device for kyphoplasty according to claim 10, wherein said sheath, in a relaxed configuration, has an axial-symmetrical configuration relative to said axis such as to substantially cover said tabs.

13. Intravertebral widening device for kyphoplasty according to claim 12, wherein said sheath, in a relaxed configuration, is at least partially separated from said tabs.

14. Intravertebral widening device for kyphoplasty according to claim 10, wherein said sheath, in a relaxed configuration, has an asymmetrical configuration relative to said extension axis such as to substantially cover said tabs.

15. Intravertebral widening device for kyphoplasty according to claim 10, wherein said sheath has a radial thickness varying along the extension axis.

16. Intravertebral widening device for kyphoplasty according to claim 15, wherein said sheath comprises a thickening near joining portions with the elastically deformable element.

17. Intravertebral widening device for kyphoplasty according to claim 15, wherein said sheath comprises a thinning between the joining portions of the sheath to the elastically deformable element.

* * * * *